United States Patent
Plos et al.

(10) Patent No.: US 6,730,133 B1
(45) Date of Patent: May 4, 2004

(54) COMPOSITIONS FOR OXIDATION DYEING OF AT LEAST ONE KERATINOUS FIBRE AND DYING PROCESSES USING THESE COMPOSITIONS

(75) Inventors: Grégory Plos, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/668,166

(22) Filed: Sep. 25, 2000

(30) Foreign Application Priority Data

Sep. 24, 1999 (FR) ............................................ 99 11967

(51) Int. Cl.$^7$ ................................................. A61K 7/13
(52) U.S. Cl. ...................... 8/405; 8/405; 8/406; 8/407; 8/409; 8/410; 8/411
(58) Field of Search ........................... 8/405, 406, 407, 8/409, 410, 411

(56) References Cited

U.S. PATENT DOCUMENTS

| | | | |
|---|---|---|---|
| 3,251,742 A | 5/1966 | Soloway | 167/88 |
| 3,893,803 A | 7/1975 | Kaiser | 8/10.2 |
| 4,003,699 A | 1/1977 | Rose et al. | 8/10.2 |
| 4,823,985 A | 4/1989 | Grollier et al. | 222/1 |
| 4,961,925 A * | 10/1990 | Tsujino et al. | 424/71 |
| 5,061,289 A | 10/1991 | Clausen et al. | 8/405 |
| 5,380,340 A | 1/1995 | Neunhoeffer et al. | 8/409 |
| 5,597,386 A * | 1/1997 | Lgarashi et al. | 8/405 |
| 5,766,576 A | 6/1998 | Löwe et al. | 424/62 |
| 5,948,121 A * | 9/1999 | Aaslyng et al. | 8/401 |
| 6,254,646 B1 * | 7/2001 | Di La Mettrie et al. | 8/406 |

FOREIGN PATENT DOCUMENTS

| | | |
|---|---|---|
| DE | 23 59 399 | 11/1973 |
| DE | 38 43 892 | 6/1990 |
| DE | 41 33 957 | 4/1993 |
| DE | 195 43 988 | 5/1997 |
| EP | 0 310 675 | 4/1989 |
| EP | 0 504 005 | 9/1992 |
| EP | 0 548 620 | 6/1993 |
| FR | 2 112 549 | 6/1972 |
| FR | 2 586 913 | 3/1987 |
| FR | 2 694 018 | 1/1994 |
| FR | 2 733 749 | 11/1996 |
| FR | 2 750 048 | 12/1997 |
| JP | 2-19576 | 1/1990 |
| WO | WO 94/08969 | 4/1994 |
| WO | WO 94/08970 | 4/1994 |
| WO | WO 95/07988 | 3/1995 |
| WO | WO 95/33836 | 12/1995 |
| WO | WO 95/33837 | 12/1995 |
| WO | WO 96/00290 | 1/1996 |
| WO | WO 96/15765 | 5/1996 |
| WO | WO 97/19998 | 6/1997 |
| WO | WO 97/19999 | 6/1997 |
| WO | WO 98/44906 | 10/1998 |

OTHER PUBLICATIONS

David Avnir et al., "Enzymes and Other Proteins Entrapped in Sol–Gel Materials", Chemistry of Materials, vol. 6, No. 10, Oct. 1994, pp. 1605–1614.

B. Dunn et al., "Strategies for Encapsulating Biomolecules in Sol–Gel Matrices", Acta Materialia, vol. 46, No. 3, Jan. 23, 1998, pp. 737–741.

English language Derwent Abstract of EP 0 504 005. Sep. 1992.

English language Derwent Abstract of EP 0 548 620. Jun. 1993.

English language Derwent Abstract of FR 2 112 549. Jun. 1972.

English language Derwent Abstract of FR 2 694 018. Jan. 1994.

English language Derwent Abstract of FR 2 733 749. Nov. 1996.

English language Derwent Abstract of FR 2 750 048. Dec. 1997.

English language Derwent Abstract of JP 2–19576. Jan. 1990.

Database Chemabs, Chemical Abstracts Service, Database Accession No. 123:296224 CA, XP002145934, 1995.

* cited by examiner

*Primary Examiner*—Margaret Einsmann
*Assistant Examiner*—Eisa Elhilo
(74) *Attorney, Agent, or Firm*—Finnegan, Henderson, Farabow, Garrett & Dunner, L.L.P.

(57) ABSTRACT

Compositions, such as ready-to-use compositions for oxidation dyeing of keratinous fibers, and in particular human keratinous fibers such as the hair, comprising, in a medium which is suitable for dyeing, at least one oxidation dye, and at least one enzymatic system, the enzymatic system comprising (i) at least one enzyme immobilized in at least one sol-gel matrix and optionally (ii) at least one suitable donor, wherein said at least one enzyme is chosen from 2-electron oxidoreductases, 4-electron oxidoreductases and peroxidases, with the proviso that when said at least one enzyme is chosen from 2-electron oxidoreductases, said at least one enzymatic system comprises at least one suitable donor, and with the proviso that when said at least one enzyme is chosen from peroxidases, said at least one enzymatic system further comprises at least one source of hydrogen peroxide chosen from hydrogen peroxide and at least one enzymatic system which generates hydrogen peroxide in situ, as well as to processes for dyeing keratinous fibers using these compositions and multicompartment device or dyeing kits comprising these compositions.

181 Claims, No Drawings

COMPOSITIONS FOR OXIDATION DYEING OF AT LEAST ONE KERATINOUS FIBRE AND DYING PROCESSES USING THESE COMPOSITIONS

The present invention relates to compositions, particularly ready-to-use compositions, for oxidation dyeing of at least one keratinous fibre, and in particular human keratinous fibres such as the hair, comprising, in a medium suitable for at least one keratinous fibre, (a) at least one oxidation dye and (b) at least one enzymatic system comprising (i) at least one enzyme immobilized in at least one matrix of material obtained via a sol-gel route (i.e., a sol-gel matrix) and optionally (ii) at least one suitable donor, wherein said at least one enzyme is chosen from 2-electron oxidoreductases, 4-electron oxidoreductases and peroxidases, such that when said at least one enzyme is chosen from 2-electron oxidoreductases, said at least one enzymatic system comprises at least one suitable donor, and when said at least one enzyme is chosen from peroxidases, said at least one enzymatic system further comprises at least one source of hydrogen peroxide chosen from hydrogen peroxide and at least one enzymatic system which generates hydrogen peroxide in situ. The present invention is also directed to processes using at least one inventive composition.

Dye compositions comprising oxidation dye precursors are known in the art for dyeing keratinous fibres, in particular human hair. These oxidation dye precursors include ortho-phenylenediamines, para-phenylenediamines, ortho-aminophenols, para-aminophenols and heterocyclic bases. These are generally known as oxidation bases. The oxidation dye precursors, or oxidation bases, are generally colorless or weakly colored compounds which may give rise to colored compounds and dyes when combined with oxidizing products via oxidative condensation.

The shades obtained with these oxidation bases may be varied by combining them with couplers or coloration modifiers. Such coloration modifiers may, for example, be chosen from aromatic meta-diamines, aromatic meta-aminophenols, aromatic meta-diphenols and certain heterocyclic compounds. The variety of oxidation bases and couplers may allow a wide range of colours to be obtained.

The so-called "permanent" coloration obtained from using these oxidation dyes should have at least one of the following desirable characteristics. The coloration should have no toxicological drawbacks, the shades obtained should have the desired intensity, and the coloration should have good resistance to external agents to which the fibres may be subjected such as light, bad weather, washing, permanent-waving, perspiration and rubbing. The dyes should allow coverage of grey hair and should be as unselective as possible, that is, they should allow only the smallest possible differences in coloration along the same keratinous fibre which may be differently sensitized (i.e. damaged) between its tip and its root.

The oxidation dyeing of at least one keratinous fibre is generally carried out in an alkaline medium in the presence of hydrogen peroxide. However, the use of alkaline media in the presence of appreciable amounts of hydrogen peroxide may result in the drawback of substantial degradation of the fibres, as well as appreciable decolorization of the keratinous fibres.

The oxidation dyeing of keratinous fibres may also be carried out using oxidizing systems other than hydrogen peroxide, such as enzymatic systems. In patent application EP-A-0 310 675, the disclosure of which is incorporated by reference, it has been proposed to dye keratinous fibres using compositions comprising an oxidation base and optionally a coupler, in combination with enzymes of the 2-electron oxidoreductase type, such as pyranose oxidase, glucose oxidase and uricase, in the presence of a donor for said enzymes. In patent applications FR-A-2 112 549, FR-A-2 694 018, EP-A-504 005, WO 95/07988, WO 95/33836, WO 95/33837, WO 96/00290, WO 97/19998, WO 97/19999, and U.S. Pat. No. 3,251,742, the disclosures of which are incorporated by reference, it has been proposed to dye keratinous fibres using compositions comprising an oxidation dye precursor and an enzyme of laccase type (4-electron oxidoreductase). Finally, it has also been proposed to dye keratinous fibres using peroxidase in the presence of small amounts of hydrogen peroxide, as has been described in patents EP-548 620, BE-775 110 and U.S. Pat. No. 3,893, 803, the disclosures of which are incorporated by reference.

Although these dyeing processes are carried out under conditions which may not result in the degradation of the keratinous fibres to the same extent as the degradation caused by dyeing keratinous fibres in the presence of appreciable amounts of hydrogen peroxide, they nonetheless may lead to colorations that are not entirely satisfactory, since interactions may exist between the dye or the various constituents of the dye support and the solvents and thickeners and/or the enzymes. These interactions may reduce the efficacy of the enzymes for dyeing the keratinous fibres. Further, another potential drawback of these dye formulations is the fact the type of enzyme used may not be sufficiently thermally stable for such dye formulations.

The inventors have discovered that when at least one oxidation dye is combined with at least one enzymatic system comprising at least one enzyme immobilized in at least one sol-gel matrix and optionally at least one suitable donor, wherein said at least one enzyme is chosen from 2-electron oxidoreductases, 4-electron oxidoreductases and peroxidases, it is possible to obtain novel powerful dyes which may display at least one of the desired qualities expressed above.

By virtue of the present invention, it may be possible to reduce the amount of enzyme used, to reduce or even prevent the interactions between the dye or the constituents of the support for the dye composition with the enzyme and it may also be possible to improve the heat stability of dye compositions comprising at least one of the aforementioned enzymes.

Specifically, one subject of the present invention is a composition for the oxidation dyeing of at least one keratinous fibre comprising, in a medium suitable for oxidation dyeing:
  (a) at least one oxidation dye; and
  (b) at least one enzymatic system comprising (i) at least one enzyme immobilized in at least one sol-gel matrix and optionally (ii) at least one suitable donor, wherein said at least one enzyme is chosen from:
    (i) 2-electron oxidoreductases;
    (ii) 4-electron oxidoreductases; and
    (iii) peroxidases;
such that when said at least one enzyme is chosen from 2-electron oxidoreductases, said at least one enzymatic system comprises at least one suitable donor, and when said at least one enzyme is chosen from peroxidases, said at least one enzymatic system further comprises at least one source of hydrogen peroxide chosen from hydrogen peroxide and at least one enzymatic system which generates hydrogen peroxide in situ, in a medium suitable for the oxidation dyeing. In one embodiment of the present invention, said composition is a ready-to-use composition. The present invention is also directed to processes for the oxidation dyeing of keratinous fibres using the inventive compositions.

As used herein, "donor" refers to the various substrates required for the corresponding enzyme to function. As used herein, "ready-to-use composition" means a composition which is intended to be applied immediately to said at least one keratinous fibre in the presence of air.

Another subject of the present invention are compositions for the oxidation dyeing of keratinous fibres comprising, in a medium suitable for at least one keratinous fibre, (a) at least one oxidation dye and (b) at least one enzymatic system comprising (i) at least one enzyme and optionally (ii) at least one suitable donor, wherein said at least one enzyme is chosen from (i) 2-electron oxidoreductases, (ii) 4-electron oxidoreductases and (iii) peroxidases, wherein said at least one oxidation dye and said at least one enzymatic system are immobilized in at least one sol-gel matrix, such that when said at least one enzyme is chosen from 2-electron oxidoreductases, said at least one enzymatic system comprises at least one suitable donor, and when said at least one enzyme is chosen from peroxidases, said at least one enzymatic system further comprises at least one source of hydrogen peroxide chosen from hydrogen peroxide and at least one enzymatic system which generates hydrogen peroxide in situ.

Yet another subject of the present invention are compositions for the oxidation dyeing of keratinous fibres comprising, in a medium suitable oxidation dyeing, (a) at least one oxidation dye and (b) at least one enzymatic system comprising (i) at least one enzyme immobilized in at least one sol-gel matrix and optionally (ii) at least one suitable donor, wherein said at least one enzyme is chosen from (i) 2-electron oxidoreductases, (ii) 4-electron oxidoreductases and (iii) peroxidases, such that when said at least one enzyme is chosen from 2-electron oxidoreductases, said at least one enzymatic system comprises at least one suitable donor, and when said at least one enzyme is chosen from peroxidases, said at least one enzymatic system further further comprises at least one source of hydrogen peroxide chosen from hydrogen peroxide and at least one enzymatic system which generates hydrogen peroxide in situ, and wherein said 4-electron oxidoreductases may optionally be combined with said at least one oxidation dye and may optionally be immobilized in said at least one sol-gel matrix.

The 2-electron oxidoreductases are suitable for use in the present invention can be chosen from pyranose oxidases, glucose oxidases, glycerol oxidases, lactate oxidases, pyruvate oxidases, uricases, choline oxidases, sarcosine oxidases, bilirubin oxidases and amino acid oxidases. Non-limiting examples of uricases suitable for use in the present invention include those of animal origin, microbiological origin and those uricases derived from biotechnology. Representative uricases are uricases extracted from boar's liver, uricases derived from *Arthrobacter globiformis* and uricases derived from *Aspergillus flavus*.

According to the present invention, the 2-electron oxidoreductases may be used in pure crystalline form or in a dilute form in an inert diluent for the 2-electron oxidoreductases. The 2-electron oxidoreductases, if present, may be present in a proportion generally ranging from about 0.01% to about 20% by weight relative to the total weight of the composition, such as from about 0.1% to about 10% by weight.

The amount of enzyme can also be defined as a function of its enzymatic activity. For example, the enzymatic activity of the 2-electron oxidoreductases in accordance with the present invention can be defined by the oxidation of a corresponding donor under aerobic conditions. According to the present invention, one U unit corresponds to the amount of enzyme sufficient to lead to the generation of one $\mu$mol of $H_2O_2$ per minute at a pH of 8.5 and at a temperature of 25° C. For example, the amount of 2-electron oxidoreductases, if present, may generally range from about 10 to about $10^8$ U units per 100 g of dye composition.

As will be recognized by one of ordinary skill in the art, the nature of the corresponding donor (or substrate) for a certain enzyme may vary as a function of the nature of the certain enzyme used. Non-limiting examples of donors include those for pyranose oxidases such as D-glucose, L-sorbose and D-xylose, donors for glucose oxidases such as D-glucose, donors for glycerol oxidases such as glycerol and dihydroxyacetone, donors for lactate oxidases such as lactic acid and its salts, donors for pyruvate oxidases such as pyruvic acid and its salts, donors for uricases such as uric acid and its salts, donors for choline oxidases such as choline and its acid addition salts for example choline hydrochloride and betaine aldehyde, donors for sarcosine oxidases such as sarcosine, N-methyl-L-leucine, N-methyl-D,L-alanine and N-methyl-D,L-valine, donors for bilirubin oxidases such as bilirubin, and donors for amino acid oxidases. Non-limiting examples of amino acid oxidases include L-amino acid oxidases and D-amino acid oxidases. Representative donors for L-amino acid oxidases are L-glycine, L-alanine, L-valine, L-phenylalanine and L-tryptophan. Representative donors for D-amino acid oxidases are D-alanine and D-phenylalanine.

The at least one suitable donor, if present, may be present in the composition in a proportion generally ranging from about 0.01% to about 20% by weight relative to the total weight of the composition, such as from about 0.1% to about 10% by weight.

According to the present invention, the 4-electron oxidoreductases can be chosen from laccases, tyrosinases, catechol oxidases, deamino oxidases and polyphenol oxidases. In one embodiment, the 4-electron oxidoreductases are chosen from laccases.

The laccases which can used according to the present invention may be chosen from laccases of plant origin, animal origin, fungal origin and bacterial origin. Additionally, the laccases may also be obtained by biotechnology. Non-limiting examples of laccases of bacterial origin include those derived from yeasts, moulds and fungi. According to the present invention, the organisms of bacterial origin may be chosen from monocellular bacteria and multicellular bacteria.

Non-limiting examples of laccases of plant origin which may be used according to the invention include laccases produced by plants performing chlorophyll synthesis, such as, for example, those mentioned in patent application FR-A-2 694 018, the disclosure of which is incorporated by reference. For example, the laccases may be chosen from those extracted from plants chosen from Anacardiacea, Podocarpacea, Rosmarinus off., *Solanum tuberosum*, Iris sp., Coffea sp., *Daucus carrota, Vinca minor, Persea americana, Catharanthus roseus*, Musa sp. *Malus pumila, Gingko biloba, Monotropa hypopithys* (Indian pipe), Aesculus sp., *Acer pseudoplatanus, Prunus persica* and *Pistacia palaestina*. Non-limiting examples of Anacardiacea are *Magnifera indica, Schinus molle* and *Pleiogynium timoriense*.

According to the present invention, laccases of fungal origin, which may optionally be obtained by biotechnology, may be chosen from those derived from fungi chosen from

*Polyporus versicolor, Rhizoctonia praticola* and *Rhus vernicifera* as described, for example, in patent applications FR-A-2 112 549 and EP-A-504 005, the disclosures of which are incorporated herein, and variants of all of the foregoing. Additional laccases are described in patent applications WO 95/07988, WO 95/33836, WO 95/33837, WO 96/00290, WO 97/19998 and WO 97/19999, the disclosures of which are incorporated herein, such as, for example, laccases chosen from those derived from fungi chosen from Scytalidium, *Polyporus pinsitus, Myceliophthora thermophila, Rhizoctonia solani, Pyricularia orizae* and variants of all of the foregoing. Further, laccases which can be used according to the present invention may be chosen from those derived from fungi chosen from *Trametes versicolor, Fomes fomentarius, Chaetomium thermophile, Neurospora crassa, Colorius versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens*, and variants of all of the foregoing.

The enzymatic activity of the laccases which can be used according to the invention and which have syringaldazine among their donors (substrates) can be defined by the oxidation of syringaldazine under aerobic conditions. According to the present invention, one Lacu unit corresponds to the amount of enzyme which is sufficient to catalyse the conversion of 1 mmol of syringaldazine per minute at a pH of 5.5 and at a temperature of 30° C. As used herein, one U unit corresponds to the amount of enzyme which is sufficient to produce an absorbance delta of 0.001 per minute at a wavelength of 530 nm, using syringaldazine as a donor (substrate), at 30° C. and at a pH of 6.5.

According to the present invention, the enzymatic activity of the laccases which can be used can also be defined by the oxidation of para-phenylenediamine. As used herein, one ulac unit corresponds to the amount of enzyme sufficient to produce an absorbance delta of 0.001 per minute at a wavelength of 496.5 nm, using para-phenylenediamine as a donor (substrate) (64 mM), at 30° C. and at a pH of 5.

Therefore, according to the present invention, when at least one laccase is present in the composition, the amount of the at least one laccase present in the composition may vary as a function of the nature of the at least one laccase used. The at least one laccase, if present, may be present in the composition in a proportion generally ranging from about 0.5 Lacu to about 2000 Lacu (i.e. generally ranging from about 10,000 U to about $40 \times 10^6$ U units or alternatively from about 20 ulac to about $20 \times 10^6$ ulac units) per 100 g of the inventive composition.

The 4-electron oxidoreductases in accordance with the present invention, if present, may be present in the composition in a proportion generally ranging from about 0.01% to about 20% by weight relative to the total weight of the composition. For example, the 4-electron oxidoreductases may be present in a proportion ranging from 0.1% to 10% by weight.

The peroxidases which can be used in the present invention may be chosen from enzymes belonging to the subclass 1.11.1 described in the book Enzyme Nomenclature, Academic Press Inc., 1984, the disclosure of which is incorporated by reference. Some of these enzymes require the presence of a corresponding donor to function. For example, the following enzymes may require such a donor: NADH peroxidases (1.11.1) (donor=NADH), fatty acid peroxidases (1.11.1.3) (donors=fatty acids, for example palmitate), NADPH peroxidases (1.11.1.2) (donor=NADPH), cytochrome-c peroxidases (1.11.1.5) (donor= ferrocytochrome c), iodide peroxidases (1.11.1.8) (donor= iodide), chloride peroxidases (1.11.10) (donor=chloride), L-ascorbate peroxidases (1.11.1.11) (donor=L-ascorbate) and glutathione peroxidases (1.11.1.9) (donor=glutathione).

According to the present invention, other peroxidases which may be used include those that function without a donor other than the oxidation dye. Non-limiting examples of such peroxidases include catalases (1.11.1.6) and simplex peroxidases (1.11.1.7). In one embodiment of the present invention, the at least one enzyme is chosen from simplex peroxidases (1.11.1.7).

All peroxidases suitable for use in the present invention require the presence of hydrogen peroxide. This hydrogen peroxide may be provided in its native form and/or generated in situ via an enzymatic route such as, for example, a 2-electron oxidase and a corresponding donor in the presence of air.

The peroxidases may be chosen from those of plant origin, animal origin, fungal origin, bacterial origin and those obtained by biotechnology. Non-limiting examples of the peroxidases which may be used in the present invention are peroxidases derived from apples, apricots, barleys, black radishes, beetroots, cabbages, carrots, corns, cottons, garlics, grapes, mints, rhubarbs, soybeans, spinach, inky caps, cow's milk and microorganisms. Representative microorganisms are Acetobacter peroxidans, Staphylococcus faecalisand Arthromycesramosus.

The unit of activity of simplex peroxidase (1.11.1.7) can be defined as being the amount of simplex enzyme sufficient to form 1 mg of purpurogallin from pyrogallol in 20 s at pH of 6 and at 20° C. For example, black radish peroxidase P6782 from Sigma (St. Louis, Mo.) has an activity of about 250 units per mg. The amount of simplex peroxidase, if present in the inventive compositions, may generally range from 25 units to $5 \times 10^6$ units per 100 g of said composition.

The peroxidases in accordance with the invention, if present, may generally be present in the composition in a proportion ranging from about 0.0001% to about 20% by weight relative to the total weight of the composition, such as from about 0.001% to about 10% by weight.

The sol-gel reaction is well known in the prior art. See C. J. Brinker and G. W. Scherer, *Sol-Gel Science*, Academic Press: New York, 1990, the disclosure of which is incorporated by reference. This is a chemical synthesis which can lead to the preparation of gels and transparent glasses from metal alkoxides. The metal alkoxides can undergo, at about room temperature, at least one partial or total hydrolysis reaction and at least one condensation polymerization to form gels.

A process involving the use of the sol-gel reaction is also known for the immobilization of biomolecules and enzymes. See B. Dunn and J. M. Miller, 46(3),737–741 (1998); see also L. M. Ellerby, *Science*, Vol. 255,1041–1180 (1992); see also D. Avnir, *Chem. Mater.*, 6,1605–1614 (1994), the disclosures of which are incorporated by reference.

The sol-gel reaction is generally carried out with at least one precursor chosen from metallic and organometallic precursors, such as those defined herein, in the presence of a sufficient amount of water which may be added and/or derived from the ambient atmospheric humidity and optionally in the presence of at least one cosmetically acceptable organic solvent.

The at least one cosmetically acceptable organic solvent which can be used according to the present invention may be chosen from lower $C_1$–$C_4$ alcohols such as ethanol, propylene glycol, propylene glycol esters, propylene glycolethers, ethylene glycol, ethylene glycol esters, ethylene glycol ethers, acetone, methyl ethyl ketone, methyl acetate, ethyl acetate, butyl acetate, glycerol, volatile hydrocarbon oils such as Isopars isoparaffins and isododecane, non-volatile hydrocarbon oils, volatile silicones such as cyclomethicones and hexamethyldisiloxanes and non-volatile silicones.

According to the present invention, the sol-gel matrix is derived from at least one sol-gel reaction of at least one precursor at a temperature suitable for said at least one sol-gel reaction, said at least one sol-gel reaction comprising (i) at least one hydrolysis reaction chosen from partial and total, and acidic and basic hydrolysis reactions, and (ii) at least one condensation reaction.

The at least one sol-gel reaction may be catalysed by acid(s) or base(s) depending on the desired properties of the final material and its intended use. The at least one partial or total hydrolysis reaction and the at least one condensation reaction may be carried out, for example, at a temperature generally ranging from 10° C. to 85° C., such as from 20° C. to 40° C.

The at least one precursor which can be used according to the present invention may be chosen from metallic and organometallic precursors. Representative metallic precursors are chosen from:

(i) oxides of transition metals from groups 1b to 7b of the Periodic Table, oxides of transition metals from group 8 of the Periodic Table and oxides of transition metals from the Lanthanide group of the Periodic Table;

(ii) aluminum oxides, boron oxides, silicon oxides and tin oxides; and (iii) aluminum phosphates.

Representative organometallic precursors are chosen from:

(1) silanes, titanates, and zirconates corresponding to compounds of formulae (Ia), (Ib), (Ic) and (Id):

$$M(OR_1)_4 \tag{Ia}$$

$$R-M(OR_1)_3 \tag{Ib}$$

$$_3(OR_1)-M-(OR_1)_3 \tag{Ic}$$

$$\begin{array}{c} R \\ \diagdown \\ M(OR_1)_2 \\ \diagup \\ R' \end{array} \tag{Id}$$

wherein:
M is chosen from silicon cations, titanium cations and zirconium cations;
$R_1$ is chosen from linear and branched alkyl groups;
R and R', which may be identical or different, are each chosen from linear and branched $C_1$–$C_{30}$ alkyl groups, $C_3$–$C_{30}$ cycloalkyl groups, aryl groups, $C_4$–$C_{30}$ aralkyl groups and $C_4$–$C_{30}$ alkylaryl groups, wherein said groups may optionally be substituted with at least one group chosen from amino groups, carboxyl groups and hydroxyl groups;

(2) chelated titanates of formula (II) and chelated zirconates of formula (II):

$$N(OR_1)_n(X)_x \tag{II}$$

wherein:
N is chosen from $Ti^{a+}$ and $Zr^{a+}$, wherein a is chosen from 4 and 6;
X, which may be identical or different, are each chosen from chelating groups, wherein the degree of complexation of said chelating groups with said N is b, and wherein b is chosen from 2 and 3;
$R_1$, which may be identical or different, are each chosen from linear and branched alkyl groups;
x is 1 or 2; and
n is equal to (a-bx), with the proviso that n is greater than or equal to 1; and (3) chelated titanates of formulae (IIIa), (IIIb) and (IIIc) and chelated zirconates of formulae (IIIa), (IIIb) and (IIIc):

$$R-N(OR_1)_m(X)_t \tag{IIIa}$$

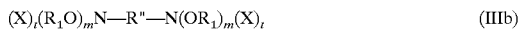
$$(X)_t(R_1O)_mN-R''-N(OR_1)_m(X)_t \tag{IIIb}$$

$$(R)(R')N(OR_1)_p(X)_t \tag{IIIc}$$

wherein:
N is chosen from $Ti^{a+}$ and $Zr^{a+}$, wherein a is chosen from 4 and 6;
X, which may be identical or different, are each chosen from chelating groups,
wherein:
the degree of complexation of said chelating groups with said N is b, wherein b is chosen from 2 and 3;
$R_1$, which may be identical or different, are each chosen from linear and branched alkyl groups;
R and R', which may be identical or different, are each chosen from linear and branched $C_1$–$C_{30}$ alkyl groups, $C_3$–$C_{30}$ cycloalkyl groups, aryl groups, $C_4$–$C_{30}$ aralkyl groups and $C_4$–$C_{30}$ alkylaryl groups, wherein said groups may optionally be substituted with at least one group chosen from amino groups, carboxyl groups and hydroxyl groups;
R" is a divalent group derived from linear and branched $C_1$–$C_{30}$ alkyl groups, $C_3$–$C_{30}$ cycloalkyl groups, aryl groups, $C_4$–$C_{30}$ aralkyl groups and $C_4$–$C_{30}$ alkylaryl groups, wherein said divalent group may optionally be substituted with at least one group chosen from amino groups, carboxyl groups and hydroxyl groups;
t is chosen from 1 and 2, except in IIIc, t may only be 1;
m is equal to (a-bt-1), with the proviso that m is greater than or equal to 1; and
p is equal to (a-bt-2), with the proviso that p is greater than or equal to 1.

In one embodiment, $R_1$ is chosen from linear and branched $C_1$–$C_4$ alkyl groups. The chelating groups may be chosen from carboxylic acids, β-ketones, β-diketones, β-keto esters, β-keto amines, α-hydroxy acids, β-hydroxy acids, amino acids such as β-hydroxyamino acids, salicylic acid and derivatives of any of the foregoing. For example, the at least one chelating group may be chosen from acetoacetoxyethyl methacrylate, methyl α-hydroxymethacrylate, ε-N-methacryloyl-L-lysine, 4-ethacrylaminosalicylic acid and 5-methacrylaminosalicylic acid.

According to the present invention, the at least one sol-gel matrix may further. comprises at least one additional optionally functionalized polymer. That is, the at least one sol-gel matrix may also be a hybrid material comprising at least one polymer network, chosen from partially crosslinked polymer networks and totally crosslinked polymer networks, derived from said at least one sol-gel reaction of said at least one precursor and at least one additional optionally functionalized polymer. The at least one additional optionally functionalized polymer can be chosen from polymers derived from radical polymerization of at least one monomer and polymers derived from polycondensation of at least one monomer.

In the present invention, the at least one additional optionally functionalized polymer can be chosen from optionally functionalized polymers which are already formed and optionally functionalized polymers formed "in situ" during the sol-gel reaction by radical polymerization or polycondensation of at least one monomer. For example, the at least one additional optionally functionalized polymer may be chosen from functionalized polymers and functionalized silicone polymers.

As used herein, "functionalized" refers to the presence of at least one functional group, wherein "functional group" refers to an atom or group of atoms that is part of a larger molecule and has a characteristic chemical reactivity. Examples of such polymers are described in patent application WO 98/44906, the disclosure of which is incorporated by reference.

In one embodiment of the present invention, the inventive composition comprises at least one sol-gel matrix derived from at least one sol-gel reaction of at least one precursor chosen from tetraalkoxysilanes, alkyltrialkoxysilanes and aminoalkyl-trialkoxysilanes at a temperature suitable for said at least one sol-gel reaction, wherein the at least one at least one precursor is reacted with water and hydrochloric acid, which are mixed together with stirring at room temperature, followed by addition of an aqueous solution of the at least one enzyme, which brings about the formation of a solid within a few minutes. This solid may then be ground up to a desired particle size.

According to the present invention, the at least one oxidation dye may be chosen from oxidation bases, couplers and the salts of any of the foregoing. For example, the oxidation bases can be chosen from para-phenylenediamines, double bases, para-aminophenols and heterocyclic bases.

Non-limiting examples of para-phenylenediamines which may be used in the present invention include those of formula (IV) and the acid addition salts thereof:

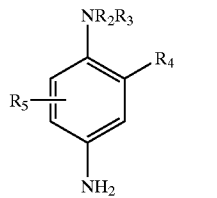

(IV)

wherein:
$R_2$ and $R_3$, which may be identical or different, are each chosen from hydrogen atoms, $C_1$–$C_4$ alkyl groups and $C_1$–$C_4$ monohydroxyalkyl groups;
$R_4$ is chosen from hydrogen atoms, halogen atoms, $C_1$–$C_4$ alkyl groups and $C_1$–$C_4$ monohydroxyalkyl groups; and
$R_5$ is chosen from hydrogen atoms and $C_1$–$C_4$ alkylgroups.

Representative para-phenylenediamines of formula (IV) are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine and N-ethyl-N-(β-hydroxyethyl)-para-phenylenediamine.

In the present invention, the double bases can be chosen from compounds comprising at least two aromatic groups substituted with at least one group chosen from amino groups and hydroxyl groups.

For example, the double bases can be chosen from compounds of formula (V) and the acid addition salts thereof:

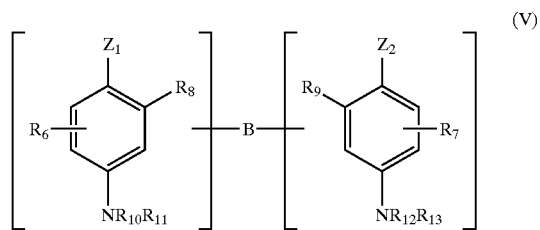

(V)

wherein:
$Z_1$ and $Z_2$, which may be identical or different, are each chosen from hydroxyl groups and —$NH_2$ groups which optionally may be substituted with at least one group chosen from $C_1$–$C_4$ alkyl groups and linking arms B;
$R_6$ and $R_7$, which may be identical or different, are each chosen from hydrogen atoms, halogen atoms, $C_1$–$C_4$ alkylgroups, $C_1$–$C_4$ monohydroxyalkylgroups, $C_2$–$C_4$ polyhydroxyalkylgroups, $C_1$–$C_4$ aminoalkylgroups and linking arms B;
$R_8$, $R_9$, $R_{10}$, $R_{11}$, $R_{12}$ and $R_{13}$, which may be identical or different, are each chosen from hydrogen atoms, $C_1$–$C_4$ alkylgroups and linking arms B; and
the linking arms B are chosen from linear and branched, divalent alkylene groups comprising from 1 to 14 carbon atoms, which may optionally be interrupted by and may optionally end with at least one group chosen from nitrogen-containing groups and hetero atoms, and which may optionally be substituted with at least one group chosen from hydroxyl groups and $C_1$–$C_6$ alkoxygroups;
with the proviso that said compounds of formula (V) comprise only one linking arm B per molecule.

Representative compounds of formula (V) are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methyl-phenyl)ethylenediamine and 1,8-bis(2,5-diaminophenoxy)-3,5-dioxaoctane. In one embodiment, the double bases of formula (V) are chosen from N,N'-bis(β-hydroxyethyl)-N,N'-bis(4'-aminophenyl)-1,3-diaminopropanol and 1,8-bis(2,5-diaminophenoxy)-3,5-dioxaoctane.

According to the present invention, para-aminophenols which can be used may be chosen from compounds of formula (VI) and the acid addition salts thereof:

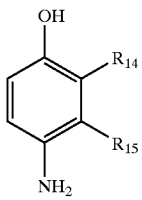
(VI)

wherein:
R$_{14}$ and R$_{15}$, which may be identical or different, are each chosen from hydrogen atoms, halogen atoms, C$_1$–C$_4$ alkyl groups, C$_1$–C$_4$ monohydroxyalkyl groups, (C$_1$–C$_4$)alkoxy(C$_1$–C$_4$)alkyl groups, C$_1$–C$_4$ aminoalkyl groups and monohydroxy(C$_1$–C$_4$)alkylamino(C$_1$–C$_4$) alkyl groups;

with the proviso that at least one of said R$_{14}$ and said R$_{15}$ is a hydrogen atom.

In one embodiment, para-aminophenols of formula (VI) are chosen from para-aminophenol, 4-amino-3-methylphenol, 4-amino-3-fluorophenol, 4-amino-3-hydroxy-methylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol.

Heterocyclic bases which can be used in accordance with the present invention comprise pyridine derivatives, pyrimidine derivatives and pyrazole derivatives. For example, pyridine derivatives may be chosen from compounds described in patents GB 1 026 978 and GB 1 153 196, the disclosures of which are incorporated by reference, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine.

In the present invention, pyrimidine derivatives which can be used may be chosen from those described, for example, in German patent DE 2 359 399 and Japanese patents JP 88-169 571 and JP 91-10659 and patent application WO 96/15765, the disclosures of which are incorporated by reference, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, pyrazolo-pyrimidine derivatives such as those mentioned in patent application FR-A-2 750 048, the disclosure of which is incorporated by reference, such as pyrazolo[1,5-a]pyrimidine-3,7-diamine, 2,5-dimethyl-pyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and the tautomeric forms of any of the foregoing when a tautomeric equilibrium exists.

According to the present invention pyrazole derivatives may be chosen from compounds described in patents DE 3 843 892 and DE 4 133 957 and patent applications WO 94/08969, WO 94/08970, FR-A-2 733 749 and DE 195 43 988, the disclosures of which are incorporated by reference, such as 4,5-diamino-1-methylpyrazole, 3,4-diaminopyrazole, 4,5-diamino-1-(4'-chlorobenzyl) pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)pyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole.

In the present invention, the couplers can be chosen from meta-aminophenols, meta-phenylenediamines, meta-diphenols, naphthols and heterocyclic couplers. Non-limiting examples of heterocyclic couplers include indole derivatives, indoline derivatives, sesamol and its derivatives, pyridine derivatives, pyrazolotriazole derivatives, and pyrazolones. For example, couplers may be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one.

In general, the acid addition salts which can be used in the present invention, such as those of oxidation bases and couplers may be chosen from hydrochlorides, hydrobromides, sulphates, tartrates, lactates and acetates of said oxidation bases and couplers.

According to the present invention, the at least one oxidation dye may be present in the composition in a proportion generally ranging from about 0.001% to about 20% by weight relative to the total weight of the composition, such as from about 0.01% to about 10% by weight.

According to the present invention, the inventive composition may further comprise at least one direct dye. This at least one direct dye may modify the shades by enriching them with glints.

As previously mentioned, the inventive compositions comprise a medium suitable for oxidation dyeing. The medium suitable for oxidation dyeing can be chosen from water and a mixture of water and at least one organic solvent if compounds are not sufficiently soluble in water alone. The at least one organic solvent may be chosen from C$_1$–C$_4$ alkanols, glycerol, glycols, glycol ethers and aromatic alcohols. Non-limiting examples of C$_1$–C$_4$ alkanols are ethanol and isopropanol, and examples of glycols and glycol ethers are 2-butoxyethanol, propylene glycol, propylene glycol monomethyl ether, diethylene glycol monoethyl ether and diethylene glycol monomethyl ether. Representative aromatic alcohols are benzyl alcohol and phenoxy ethanol.

The proportion of the at least one organic solvent, if present, generally ranges from about 1% to about 40% by weight relative to the total weight of the composition, such as from about 5% to about 30% by weight.

According to the present invention, the pH of the inventive composition can be chosen such that the enzymatic activity of the at least one enzyme is sufficient. The pH of said composition generally ranges from about 3 to about 11, such as from about 4 to about 9. The pH may be adjusted to the desired value using acidifying or basifying agents suitable for use in compositions for dyeing of keratinous fibres.

Acidifying agents which may used according to the present invention can be chosen from inorganic acids and organic acids. For example, the acidifying agents can be chosen from hydrochloric acid, orthophosphoric acid, sulphuric acid, carboxylic acids such as acetic acid, tartaric acid, citric acid and lactic acid and sulphonic acids.

Basifying agents which may be used according to the present invention can be chosen from aqueous ammonia, alkaline carbonates, alkanolamines such as mono-ethanolamines, di-ethanolamines and tri-ethanolamines, 2-methyl-2-amino-1-propanol and derivatives thereof, sodium hydroxide, potassium hydroxide and compounds of formula (VII):

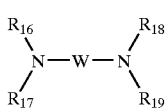

(VII)

wherein:
W is chosen from propylene groups, optionally substituted with at least one group chosen from hydroxyl groups and $C_1$–$C_4$ alkyl groups; and
$R_{16}$, $R_{17}$, $R_{18}$ and $R_{19}$, which may be identical or different, are each chosen from hydrogen atoms, $C_1$–$C_4$ alkyl groups and $C_1$–$C_4$ hydroxyalkyl groups.

According to the present invention, the compositions can further comprise at least one suitable additive chosen from anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickeners, organic thickeners, antioxidants, penetrating agents, sequestering agents, fragrances, buffers, dispersants, conditioners such as, for example, volatile and non-volatile, modified and unmodified silicones, film-forming agents, ceramides, preserving agents, opacifiers and any other additive conventionally used in dye compositions.

Needless to say, a person skilled in the art will take care to select the at least one suitable additive such that the advantageous properties of the composition in accordance with the invention are not, or are not substantially, adversely affected by the addition(s) envisaged.

In the present invention, the inventive compositions can be in the form of liquids, creams, mousses or gels, which may optionally be pressurized, or in any other form which is suitable for at least one keratinous fibre, such as human hair.

According to the present invention, where the at least one oxidation dye and at least one enzyme chosen from 2-electron oxidoreductases and 4-electron oxidoreductases are present in the composition, said composition should be stored before use such that it is substantially free of oxygen gas, so as to avoid any premature oxidation of said at least one oxidation dye.

As previously mentioned, another subject of the present invention are processes for dyeing at least one keratinous fibre using at least one inventive composition as defined above. According to one inventive process, at least one composition as defined above is applied to said at least one keratinous fibre at a temperature and for a time sufficient to develop a desired coloration. The at least one keratinous fibre may then optionally be rinsed, be washed with shampoo and/or be dried. The application temperature according to the present invention generally ranges from room temperature to 60° C., such as from room temperature to 45° C., and further such as from 20° C. to 37° C. The time sufficient to develop a desired coloration of said keratinous fibres according to the present invention may generally range 1 minute to 60 minutes, such as from 5 minutes to 30 minutes.

Yet another subject of the present invention are processes for dyeing at least one keratinous fibre comprising the steps of (A) storing, in the absence of air, at least one composition comprising (a) at least one oxidation dye and (b) at least one enzymatic system comprising (i) at least one enzyme immobilized in at least one sol-gel matrix and optionally (ii) at least one suitable donor, wherein said at least one enzyme is chosen from:
(i) 2-electron oxidoreductases;
(ii) 4-electron oxidoreductases; and
(iii) peroxidases;
in a medium suitable for at least one keratinous fibre, such that when said at least one enzyme is chosen from 2-electron oxidoreductases, said at least one enzymatic system comprises at least one suitable donor, and when said at least one enzyme is chosen from peroxidases, said at least one enzymatic system further comprises at least one source of hydrogen peroxide chosen from hydrogen peroxide and at least one enzymatic system which generates hydrogen peroxide in situ, and (B) applying said at least one composition to said at least one keratinous fibre in the presence of air and for a time and at a temperature sufficient to develop a desired coloration.

Another subject of the present invention is processes for dyeing at least one keratinous fibre comprising the steps of (A) storing, in the absence of air, at least one sol-gel matrix comprising at least one composition comprising (a) at least one oxidation dye and (b) at least one enzymatic system comprising (i) at least one enzyme immobilized in said at least one sol-gel matrix and optionally (ii) at least one suitable donor, wherein said at least one enzyme is chosen from:
(i) 2-electron oxidoreductases;
(ii) 4-electron oxidoreductases; and
(iii) peroxidases;
such that when said at least one enzyme is chosen from 2-electron oxidoreductases, said at least one enzymatic system comprises at least one suitable donor, and when said at least one enzyme is chosen from peroxidases, said at least one enzymatic system further further comprises at least one source of hydrogen peroxide chosen from hydrogen peroxide and at least one enzymatic system which generates hydrogen peroxide in situ, (B) dispersing said at least one sol-gel matrix in a medium suitable for oxidation dyeing, and (C) applying said at least one sol-gel matrix dispersed in said medium suitable for oxidation dyeing to said keratinous fibres in the presence of air and for a time and at a temperature sufficient to develop a desired coloration.

The present invention is also directed to processes for dyeing keratinous fibres comprising (a) storing a first composition, (b) storing a second composition separately from said first composition and said third composition, (c) optionally storing a third composition separately from said first composition and said second composition, (d) mixing said first composition, said second composition and optionally said third composition to form a mixture in the presence of air and (e) applying said mixture to said keratinous fibres for a time and at a temperature sufficient to develop a desired coloration.

Further, another subject of the present invention is multicompartment devices or dyeing kits comprising (a) a first compartment comprising a first composition and optionally at least one suitable donor for said peroxidases and (b) a second compartment comprising a second composition, wherein said first compartment comprises at least one oxidation dye in a medium suitable for keratinous fibres, and wherein said second compartment comprises at least one enzymatic system comprising (i) at least one enzyme immobilized in at least one sol-gel matrix and optionally (ii) at least one suitable donor, wherein said at least one enzyme is chosen from:

(i) 2-electron oxidoreductases;
(ii) 4-electron oxidoreductases; and
(ii) peroxidases;

in a medium suitable for oxidation dyeing, such that when said at least one enzyme is chosen from 2-electron oxidoreductases, said at least one enzymatic system comprises at least one suitable donor, and when said at least one enzyme is chosen from peroxidases, said at least one enzymatic system further further comprises at least one source of hydrogen peroxide chosen from hydrogen peroxide and at least one enzymatic system which generates hydrogen peroxide in situ, in a medium suitable for oxidation dyeing.

The present invention is also directed to multicompartment devices or dyeing kits comprising (a) a first compartment comprising a first composition, (b) a second compartment comprising a second composition and (c) a third compartment comprising a third composition, wherein said first compartment comprises at least one oxidation dye, in a medium suitable for oxidation dyeing, wherein said second compartment comprises at least one enzymatic system comprising (i) at least one enzyme immobilized in at least one sol-gel matrix chosen from 2-electron oxidoreductases and (ii) at least one source of hydrogen peroxide chosen from hydrogen peroxide and at least one enzymatic system which generates hydrogen peroxide in situ, in a medium suitable for oxidation dyeing, and wherein said third compartment comprises at least one suitable donor for said at least one enzyme.

Another subject of the present invention is multicompartment devices or dyeing kits comprising (a) a first compartment comprising a first composition, (b) a second compartment comprising a second composition and (c) a third compartment comprising a third composition, wherein said first compartment comprises at least one oxidation dye and optionally at least one suitable donor, in a medium suitable for oxidation dyeing, wherein said second compartment comprises at least one enzymatic system comprising at least one 2-electron oxidoreductase immobilized in at least one sol-gel matrix, at least one peroxidase immobilized in at least one sol-gel matrix and optionally at least one suitable donor, in a medium suitable for oxidation dyeing and wherein said third compartment comprises at least one suitable donor chosen from 2-electron oxidoreductase donors and peroxidase donors, in a medium suitable for oxidation dyeing.

Another subject of the present invention is multicompartment devices or dyeing kits comprising (a) a first compartment comprising a first composition, (b) a second compartment comprising a second composition and (c) a third compartment comprising a third composition, wherein said first compartment comprises at least one oxidation dye and optionally at least one suitable donor, in a medium suitable for oxidation dyeing, wherein said second compartment comprises at least one enzymatic system comprising at least one peroxidase immobilized in at least one sol-gel matrix and optionally at least one suitable donor, in a medium suitable for oxidation dyeing, and wherein said third compartment comprises at least one source of hydrogen peroxide chosen from (i) 2-electron oxidoreductases immobilized in at least one sol-gel matrix and optionally at least one suitable donor and (ii) hydrogen peroxide solutions, in a medium suitable for at least one keratinous fibre.

All of the aforementioned devices may be equipped with a means for applying the desired mixture to at least one keratinous fibre, such as the devices described in patent FR-2 586 913, the disclosure of which is incorporated by reference.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

EXAMPLE 1

Preparation of Immobilized Uricase 8 grams of tetramethoxysilane were, mixed with 3 grams of water and 0.2 gram of 0.04 molar hydrochloric acid solution. After stirring for twenty minutes at room temperature, a homogeneous solution was obtained. 11.2 grams of an aqueous solution of *Arthrobacter globiformis* uricase at a concentration of 20 I.U./mg, sold by the company Sigma at $1 \times 10^6$ U %, was added to this solution. After a few minutes, a hard, brittle solid was obtained. The solid obtained was ground up, washed with deionized water and then dried to give a crystalline powder.

EXAMPLE 2

Preparation of Immobilized Iaccase 40 grams of tetramethoxysilane were mixed with 0.5 gram of a 0.04 molar hydrochloric acid solution. After stirring for twenty minutes at room temperature, a homogeneous solution was obtained. An aqueous solution of laccase SP809 at a concentration of $10 \times 10^6$ units U, sold by the company Novo Nordisk (Denmark) and having $6 \times 10^8$ U %, was added to this solution. After a few minutes, a hard, brittle solid was obtained. The solid obtained was ground, washed with deionized water and then dried to give a crystalline powder.

EXAMPLE 3

Dye Composition

The following dye composition was prepared:

| | |
|---|---|
| para-Phenylenediamine dihydrochloride | 1.0 g |
| N-Acetylcysteine | 0.10 g |
| 6-Methoxybenzo[1,3]dioxol-5-ylamine hydrochloride | 0.71 g |
| 1-β-Hydroxyethyloxy-2,4-diaminobenzene dihydrochloride | 0.88 g |
| Immobilized Uricase of Example 1 | 4.0 g |
| Uric acid | 1.0 g |
| Polyglyceryl monooleate sold under the name Decaglyn 1-0 by the company Nikko | 1.0 g |
| Aculyn 22 from the company Röhm & Haas* | 0.75 g AM** |
| 2-Amino-2-methyl-1-propanol qs pH | 9.5 |
| Demineralized water qs | 100 g |

*Oxyethylenated methacrylic acid/ethyl acrylate/stearyl methacrylate terpolymer (55/35/10) as an aqueous 30% dispersion
**denotes Active Material This composition was prepared at the time of use by mixing the 4 grams of immobilized uricase with the rest of the composition and was applied to natural grey hair containing 90% white hairs.

After leaving the composition to stand on the hair for 30 minutes, the hair was rinsed, washed with a standard shampoo and then dried.

The hair was dyed in an intense black shade.

EXAMPLE 4

Dye Composition

The following dye composition was prepared:

| | |
|---|---|
| 4-Aminophenol | 0.11 g |
| N-Acetylcysteine | 0.10 g |
| 2-Methyl-5-aminophenol | 0.12 g |
| Immobilized Uricase of Example 1 | 4.0 g |
| Uric acid | 1.0 g |
| Polyglyceryl monooleate sold under the name Decaglyn 1-0 by the company Nikko | 1.0 g |
| Aculyn 22 from the company Röhm & Haas* | 0.75 g AM** |
| 2-Amino-2-methyl-1-propanol qs pH | 9.5 |
| Demineralized water qs | 100 g |

*Oxyethylenated methacrylic acid/ethyl acrylate/stearyl methacrylate terpolymer (55/35/10) as an aqueous 30% dispersion
**denotes Active Material This composition was prepared at the time of use by mixing the 4 grams of immobilized uricase with the rest of the composition and was applied to natural grey hair containing 90% white hairs.

After leaving the composition to stand on the hair for 30 minutes, the hair was rinsed, washed with a standard shampoo and then dried.

The hair was dyed in an intense coppery-golden shade.

EXAMPLE 5

Dye Composition

The following dye composition was prepared:

| | |
|---|---|
| para-Phenylenediamine dihydrochloride | 0.18 g |
| N-Acetylcysteine | 0.10 g |
| 6-Hydroxybenzomorpholine | 0.15 g |
| Immobilized laccase of Example 2 | 2.8 g |
| Polyglyceryl monooleate sold under the name Decaglyn 1-0 by the company Nikko | 1.0 g |
| Aculyn 22 from the company Röhm & Haas* | 0.75 g AM** |
| 2-Amino-2-methyl-1-propanol qs pH | 7 |
| Demineralized water qs | 100 g |

*Oxyethylenated methacrylic acid/ethyl acrylate/stearyl methacrylate terpolymer (55/35/10) as an aqueous 30% dispersion
**denotes Active Material This composition was prepared at the time of use by mixing the 2.8 grams of immobilized laccase with the rest of the composition and was applied to natural grey hair containing 90% white hairs.

After leaving the composition to stand on the hair for 30 minutes, the hair was rinsed, washed with a standard shampoo and then dried.

The hair was dyed in an intense natural ash shade.

EXAMPLE 6

Dye Composition

The following dye composition was prepared:

| | |
|---|---|
| para-Phenylenediamine dihydrochloride | 0.18 g |
| N-Acetylcysteine | 0.10 g |
| 2-Methyl-5-aminophenol | 0.12 g |
| Immobilized laccase of Example 2 | 2.8 g |
| Polyglyceryl monooleate sold under the name Decaglyn 1-0 by the company Nikko | 1.0 g |
| Aculyn 22 from the company Röhm & Haas* | 0.75 g AM** |
| 2-Amino-2-methyl-1-propanol qs pH | 7 |
| Demineralized water qs | 100 g |

*Oxyethylenated methacrylic acid/ethyl acrylate/stearyl methacrylate terpolymer (55/35/10) as an aqueous 30% dispersion
**denotes Active Material This composition was prepared at the time of use by mixing the 2.8 grams of immobilized laccase with the rest of the composition and was applied to natural grey hair containing 90% white hairs.

After leaving the composition to stand on the hair for 30 minutes, the hair was rinsed, washed with a standard shampoo and then dried.

The hair was dyed in a violet shade.

What we claim is:

1. A composition for the oxidation dyeing of keratinous fibres comprising:
   (a) at least one oxidation dye; and
   (b) at least one enzymatic system comprising (i) at least one sol-gel matrix and at least one enzyme immobilized in said at least one sol-gel matrix and optionally (ii) at least one donor for said at least one enzyme, wherein said at least one enzyme is chosen from:
   (i) 2-electron oxidoreductases;
   (ii) 4-electron oxidoreductases; and
   (iii) peroxidases;
   with the proviso that when said at least one enzyme is chosen from 2-electron oxidoreductases, said at least one enzymatic system comprises at least one donor for said at least one enzyme, and with the proviso that when said at least one enzyme is chosen from peroxidases, said at least one enzymatic system further comprises at least one source of hydrogen peroxide chosen from hydrogen peroxide and at least one enzymatic system which generates hydrogen peroxide in situ, in a medium suitable for said oxidation dyeing.

2. A composition according to claim 1, wherein said keratinous fibres are human keratinous fibres.

3. A composition according to claim 2, wherein said human keratinous fibres are hair.

4. A composition according to claim 1, wherein said composition is a ready-to-use composition.

5. A composition according to claim 1, wherein said at least one oxidation dye and said at least one enzymatic system are immobilized in the at least one sol-gel matrix.

6. A composition according to claim 1, wherein said at least one enzyme is chosen from 4-electron oxidoreductases and said at least one enzyme is combined with said at least one oxidation dye.

7. A composition according to claim 1, wherein said sol-gel matrix is derived from at least one sol-gel reaction of at least one precursor at a temperature suitable for said at least one sol-gel reaction, said at least one sol-gel reaction comprising (i) at least one hydrolysis reaction chosen from partial and total, acidic and basic hydrolysis reactions, and (ii) at least one condensation reaction.

8. A composition according to claim 7, wherein said temperature suitable for said at least one sol-gel reaction ranges from about 10° C. to about 85° C.

9. A composition according to claim 8, wherein said temperature suitable for said at least one sol-gel reaction ranges from about 20° C. to about 40° C.

10. A composition according to claim 7, wherein said at least one precursor is chosen from metallic precursors, wherein said metallic precursors are chosen from:

(i) oxides of transition metals, wherein said oxides of transition metals are chosen from oxides of transition metals of groups 1b to 7b of the Periodic Table, oxides of transition metals of group 8 and oxides of transition metals of the Lanthanide group of the Periodic Table;

(ii) aluminum oxides, boron oxides, silicon oxides and tin oxides; and (iii) aluminum phosphates.

11. A composition according to claim 7, wherein said at least one precursor is chosen from organometallic precursors wherein said organometallic precursors are chosen from:

(1) silanes, titanates, and zirconates of formulae (Ia), (Ib), (Ic) and (Id):

M(OR$_1$)$_4$                                                             (Ia)

R—M(OR$_1$)$_3$                                                  (Ib)

$_3$(OR$_1$)—M—(OR$_1$)$_3$                                   (Ic)

$$\begin{array}{c} R \\ \diagdown \\ M(OR_1)_2 \\ \diagup \\ R' \end{array}$$                    (Id)

wherein:

M is chosen from silicon cations, titanium cations and zirconium cations;

R$_1$ is chosen from linear and branched alkyl groups;

R and R', which may be identical or different, are each chosen from linear and branched C$_1$–C$_{30}$ alkyl groups, C$_3$–C$_{30}$ cycloalkyl groups, aryl groups, C$_4$–C$_{30}$ aralkyl groups and C$_4$–C$_{30}$ alkylaryl groups, wherein said groups may optionally be substituted with at least one group chosen from amino groups, carboxyl groups and hydroxyl groups;

(2) chelated titanates of formula (II) and chelated zirconates of formula (II):

N(OR$_1$)$_n$(X)$_x$                                                         (II)

wherein:

N is chosen from Ti$^{a+}$ and Zr$^{a+}$, wherein:

a is chosen from 4 and 6;

X, which may be identical or different, are each chosen from chelating groups, wherein:

the degree of complexation of said chelating groups with said N is b;

wherein:

b is chosen from 2 and 3;

R$_1$, which may be identical or different, are each chosen from linear and branched alkyl groups;

x is 1 or 2; and n is equal to (a-bx) with the proviso that n is greater than or equal to 1; and (3) chelated titanates of formulae (IIIa), (IIIb) and (IIIc) and chelated zirconates of formulae (IIIa), (IIIb) and (IIIc):

R—N(OR$_1$)$_m$(X)$_t$                                      (IIIb)

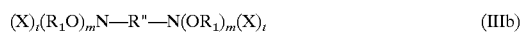

(X)$_t$(R$_1$O)$_m$N—R"—N(OR$_1$)$_m$(X)$_t$        (IIIb)

(R)(R')N(OR$_1$)$_p$(X)$_t$                                   (IIIc)

wherein:

N is chosen from Ti$^{a+}$ and Zr$^{a+}$, wherein a is chosen from 4 and 6;

X, which may be identical or different, are each chosen from chelating groups, wherein:

the degree of complexation of said chelating groups with said N is b, wherein b is chosen from 2 and 3;

R$_1$, which may be identical or different, are each chosen from linear and branched alkyl groups;

R and R', which may be identical or different, are each chosen from linear and branched C$_1$–C$_{30}$ alkyl groups, C$_3$–C$_{30}$ cycloalkyl groups, aryl groups, C$_4$–C$_{30}$ aralkyl groups and C$_4$–C$_{30}$ alkylaryl groups, wherein said groups may optionally be substituted with at least one group chosen from amino groups, carboxyl groups and hydroxyl groups;

R" is a divalent group derived from linear and branched C$_1$–C$_{30}$ alkyl groups, C$_3$–C$_{30}$ cycloalkyl groups, aryl groups, C$_4$–C$_{30}$ aralkyl groups and C$_4$–C$_{30}$ alkylaryl groups, wherein said divalent group may optionally be substituted with at least one group chosen from amino groups, carboxyl groups and hydroxyl groups;

t is chosen from 1 and 2, except in IIIc, t may only be 1;

m is equal to (a-bt-1), with the proviso that m is greater than or equal to 1; and p is equal to (a-bt-2), with the proviso that p is greater than or equal to 1.

12. A composition according to claim 11, wherein said $R_1$ is chosen from linear and branched $C_1$–$C_4$ alkyl groups.

13. A composition according to claim 11, wherein said chelating groups are chosen from carboxylic acids, β-ketones, β-diketones, β-keto esters, β-keto amines, α-hydroxy acids, β-hydroxy acids, amino acids, salicylic acid and derivatives of any of the foregoing.

14. A composition according to claim 13, wherein said chelating groups are chosen from acetoacetoxyethyl methacrylate, methyl α-hydroxymethacrylate, ε-N-methacryloyl-L-lysine, 4-ethacrylaminosalicylic acid and 5-methacrylaminosalicylic acid.

15. A composition according to claim 7, wherein said at least one precursor is chosen from tetraalkoxysilanes, alkyltrialkoxysilanes and aminoalkyltrialkoxysilanes.

16. A composition according to claim 7, wherein said at least one sol-gel matrix further comprises at least one additional optionally functionalized polymer.

17. A composition according to claim 16, wherein said at least one sol-gel matrix comprises at least one polymer network, chosen from partially crosslinked polymer networks and totally crosslinked polymer networks, derived from said at least one sol-gel reaction of said at least one precursor and at least one additional optionally functionalized polymer.

18. A composition according to claim 17, wherein said at least one additional optionally functionalized polymer is chosen from polymers derived from radical polymerization of at least one monomer and polymers derived from polycondensation of at least one monomer.

19. A composition according to claim 1, wherein said 2-electron oxidoreductases, which may be identical or different, are each chosen from pyranose oxidases, glucose oxidases, glycerol oxidases, lactate oxidases, pyruvate oxidases, uricases, choline oxidases, sarcosine oxidases, bilirubin oxidases and amino acid oxidases.

20. A composition according to claim 19, wherein said uricases are chosen from uricases of animal origin, microbial origin and those uricases derived from biotechnology.

21. A composition according to claim 19, wherein said uricases are chosen from uricases extracted from boar's liver, uricases derived from *Arthrobacter globiformis* and uricases derived from *Aspergillus flavus*.

22. A composition according to claim 1, wherein said 2-electron oxidoreductases, which may be identical or different, are present in said composition in an amount ranging from about 0.01% to about 20% by weight relative to the total weight of said composition.

23. A composition according to claim 22, wherein said 2-electron oxidoreductases, which may be identical or different, are present in said composition in an amount ranging from about 0.1% to about 10% by weight relative to the total weight of said composition.

24. A composition according to claim 1, wherein said 2-electron oxidoreductases, which may be identical or different, are present in said composition in an amount ranging from about 10 U to about $10^8$ U units per 100 g of dye composition.

25. A composition according claim 1, wherein said 4-electron oxidoreductases, which may be identical or different, are chosen from laccases, tyrosinases, catechol oxidases, deamino oxidases and polyphenol oxidases.

26. A composition according to claim 25, wherein said 4-electron oxidoreductases, which may be identical or different, are each chosen from laccases of plant origin, animal origin, fungal origin and bacterial origin and laccases obtained by biotechnology.

27. A composition according to claim 26, wherein said laccases are chosen from those produced by plants performing chlorophyll synthesis.

28. A composition according to claim 26, wherein said laccases are chosen any of the laccases which may be extracted from Anacardiacea, Podocarpacea, Rosmarinus off., *Solanum tuberosum*, Iris sp., Coffea sp., *Daucus carrota*, *Vinca minor*, *Persea americana*, *Catharanthus roseus*, Musa sp., *Malus pumila*, *Gingko biloba*, *Monotropa hypopithys*, Aesculus sp., *Acer pseudoplatanus*, *Prunus persica* and *Pistacia palaestina*.

29. A composition according to claim 26, wherein said laccases are chosen from those of fungal origin and those obtained by biotechnology.

30. A composition according to claim 29, wherein said laccases are chosen from *Polyporus versicolor*, *Rhizoctonia praticola*, *Rhus vernicifera*, Scytalidium, *Polyporus pinsitus*, *Myceliophthora thermophila*, *Rhizoctonia solani*, *Pyricularia orizae*, *Trametes versicolor*, *Fomes fomentarius*, *Chaetomium thermophile*, *Neurospora crassa*, *Colorius versicol*, *Botrytis cinerea*, *Rigidoporus lignosus*, *Phellinus noxius*, *Pleurotus ostreatus*, *Aspergillus nidulans*, *Podospora anserina*, *Agaricus bisporus*, *Ganoderma lucidum*, *Glomerella cingulata*, *Lactarius piperatus*, *Russula delica*, *Heterobasidion annosum*, *Thelephora terrestris*, *Cladosporium cladosporioides*, *Cerrena unicolor*, *Coriolus hirsutus*, *Ceriporiopsis subvermispora*, *Coprinus cinereus*, *Panaeolus papilionaceus*, *Panaeolus sphinctrinus*, *Schizophyllum commune*, *Dichomitius squalens* and variants of any of the foregoing.

31. A composition according to claim 26, wherein said laccases are present in said composition in an amount ranging from about 0.5 lacu to about 2000 lacu units per 100 g of said composition.

32. A composition according to claim 26, wherein said laccases are present in said composition in an amount ranging from about 10,000 U to about $4\times10^7$ U units per 100 g of said composition.

33. A composition according to claim 26, wherein said laccases are present in said composition in an amount ranging from about 20 ulac to about $2\times10^6$ ulac units per 100 g of said composition.

34. A composition according to claim 1, wherein said 4-electron oxidoreductases are present in said composition in an amount ranging from about 0.01% to about 20% by weight relative to the total weight of said composition.

35. A composition according to claim 34, wherein said 4-electron oxidoreductases are present in said composition in an amount ranging from about 0.1% to about 10% by weight relative to the total weight of said composition.

36. A composition according claim 1, wherein said peroxidases, which may be identical or different, are each chosen from NADH peroxidases, fatty acid peroxidases, NADPH peroxidases, cytochrome-c peroxidases, iodide peroxidases, chloride peroxidases, L-ascorbate peroxidases and glutathione peroxidases.

37. A composition according to claim 1, wherein said peroxidases, which may be identical or different, are each chosen from simplex peroxidases and catalases.

38. A composition according claim 37, wherein said peroxidases, which may be identical or different, are each chosen from simplex peroxidases.

39. A composition according claim 1, wherein said peroxidases, which may be different or identical, are each chosen from peroxidases of animal origin, plant origin, fungal origin bacterial origin and those peroxidases obtained by biotechnology.

40. A composition according to claim 39, wherein said peroxidases, which may be identical or different, are each chosen from peroxidases extracted from apples, peroxidases extracted from apricots, peroxidases extracted from barleys, peroxidases extracted from black radishes, peroxidases extracted from beetroots, peroxidases extracted from cabbages, peroxidases extracted from carrots, peroxidases extracted from corns, peroxidases extracted from cottons, peroxidases extracted from garlics, peroxidases extracted from grapes, peroxidases extracted from mints, peroxidases extracted from rhubarbs, peroxidases extracted from soybeans, peroxidases extracted from spinach, peroxidases extracted from inky cap, peroxidases extracted from cow's milk and peroxidases extracted from microorganisms.

41. A composition according to claim 42, wherein said microorganisms are chosen from *Acetobacter peroxidans, Staphylococcus faecalis* and Arthromycesramosus.

42. A composition according to claim 1, wherein said peroxidases, which may be different or identical, are present in said composition in an amount ranging from about 0.0001% to about 20% by weight relative to the total weight of said composition.

43. A composition according to claim 42, wherein said peroxidases, which may be different or identical, are present in said composition in an amount ranging from about 0.001% to about 10% by weight relative to the total weight of said composition.

44. A composition according to claim 7, wherein said at least one sol-gel reaction further comprises at least one step chosen from addition of at least one cosmetically acceptable organic solvent and dissolving said at least one precursor in at least one cosmetically acceptable organic solvent optionally comprising water.

45. A composition according to claim 44, wherein said at least one cosmetically acceptable organic solvent is chosen from lower $C_1$–$C_4$ alcohols, propylene glycol, propylene glycol esters, propylene glycolethers, ethylene glycol, ethylene glycol esters, ethylene glycol ethers, acetone, methyl ethyl ketone, methyl acetate, ethyl acetate, butyl acetate, glycerol, volatile hydrocarbon oils, non-volatile hydrocarbon oils, volatile silicones and non-volatile silicones.

46. A composition according to claim 45, wherein said lower $C_1$–$C_4$ alcohols are chosen from ethanol.

47. A composition according to claim 45, wherein said volatile hydrocarbon oils are chosen from Isopars isoparaffins and isododecane.

48. A composition according to claim 45, wherein said volatile silicones are chosen from cyclomethicones and hexamethyldisiloxanes.

49. A composition according claim 1, wherein said at least one oxidation dye is chosen from oxidation bases, couplers and acid addition salts of any of the foregoing.

50. A composition according to claim 49, wherein said acid addition salts are chosen from hydrochlorides, hydrobromides, sulphates, tartrates, lactates and acetates.

51. A composition according to claim 49, wherein said oxidation bases are chosen from para-phenylenediamines, double bases, para-aminophenols and heterocyclic bases.

52. A composition according to claim 51, wherein said para-phenylenediamines are chosen from compounds having formula (IV) and the acid addition salts thereof:

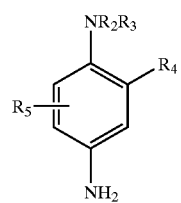

(IV)

wherein:
$R_2$ and $R_3$, which may be identical or different, are each chosen from hydrogen atoms, $C_1$–$C_4$ alkyl groups and $C_1$–$C_4$ monohydroxyalkyl groups;
$R_4$ is chosen from hydrogen atoms, halogen atoms, $C_1$–$C_4$ alkyl groups and $C_1$–$C_4$ monohydroxyalkyl groups; and
$R_5$ is chosen from hydrogen atoms and $C_1$–$C_4$ alkyl-groups.

53. A composition according to claim 52, wherein said para-phenylenediamines of formula (IV) are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis($\beta$-hydroxyethyl)-para-phenylenediamine, 4-N,N-bis($\beta$-hydroxyethyl)amino-2-methylaniline, 4-N,N-bis($\beta$-hydroxyethyl)amino-2-chloroaniline, 2-$\beta$-hydroxyethyl-para-phenylenediamine, 2-fluoro-para-phenylenediamine, 2-isopropyl-para-phenylenediamine, N-($\beta$-hydroxypropyl)-para-phenylenediamine, 2-hydroxymethyl-para-phenylenediamine, N,N-dimethyl-3-methyl-para-phenylenediamine and N-ethyl-N-($\beta$-hydroxyethyl)-para-phenylenediamine.

54. A composition according to claim 51, wherein said double bases are chosen from compounds of formula (V) and the acid addition salts thereof:

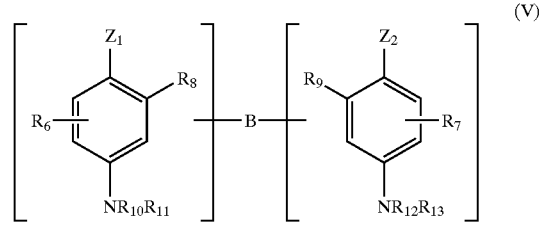

(V)

wherein:
$Z_1$ and $Z_2$, which may be identical or different, are each chosen from hydroxyl groups and —$NH_2$ groups which optionally may be substituted with at least one group chosen from $C_1$–$C_4$ alkyl groups and linking arms B;
$R_6$ and $R_7$, which may be identical or different, are each chosen from hydrogen atoms, halogen atoms, $C_1$–$C_4$ alkylgroups, $C_1$–$C_4$ monohydroxyalkylgroups, $C_2$–$C_4$ polyhydroxyalkylgroups, $C_1$–$C_4$ aminoalkylgroups and linking arms B;
$R_8$, $R_9$, $R_{10}$, $R_{11}$, $R_{12}$ and $R_{13}$, which may be identical or different, are each chosen from hydrogen atoms, $C_1$–$C_4$ alkylgroups and linking arms B; and
the linking arms B are chosen from linear and branched, divalent alkylene groups comprising from 1 to 14 carbon atoms, which may optionally be interrupted by and may optionally end with at least one group chosen from nitrogen-containing groups and hetero atoms, and which may optionally be substituted with at least one group chosen from hydroxyl groups and $C_1$–$C_6$ alkoxygroups;

with the proviso that said compounds of formula (V) comprise only one linking arm B per molecule.

55. A composition according to claim 54, wherein said hetero atoms are chosen from oxygen atoms, sulphur atoms and nitrogen atoms.

56. A composition according to claim 54, wherein said nitrogen-containing groups are chosen from amino groups, mono($C_1$–$C_4$)alkylamino groups, di($C_1$–$C_4$)alkylamino groups, tri($C_1$–$C_4$)alkylamino groups, monohydroxy ($C_1$–$C_4$)alkylamino groups, imidazolinium groups and ammonium groups.

57. A composition according to claim 56, wherein said double bases of formula (V) are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane.

58. A composition according to claim 57, wherein said double bases of formula (V) are chosen from N,N'-bis(β-hydroxyethyl)-N,N'-bis(4'-aminophenyl)-1,3-diaminopropanol and 1,8-bis(2,5-diaminophenoxy)-3,5-dioxaoctane.

59. A composition according to claim 51, wherein said para-aminophenols are chosen from compounds of formula (VI) and the acid addition salts thereof:

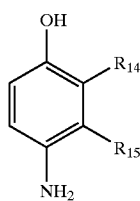

(VI)

wherein:

$R_{14}$ and $R_{15}$, which may be identical or different, are each chosen from hydrogen atoms, halogen atoms, $C_1$–$C_4$ alkyl groups, $C_1$–$C_4$ monohydroxyalkyl groups, ($C_1$–$C_4$)alkoxy($C_1$–$C_4$)alkyl groups, $C_1$–$C_4$ aminoalkyl groups and monohydroxy($C_1$–$C_4$)alkylamino($C_1$–$C_4$) alkyl groups;

with the proviso that at least one of said $R_{14}$ and said $R_{15}$ is a hydrogen atom.

60. A composition according to claim 59, wherein said para-aminophenols of formula (VI) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and 4-amino-2-fluorophenol.

61. A composition according to claim 51, wherein said heterocyclic bases are chosen from pyridine derivatives, pyrimidine derivatives and pyrazole derivatives.

62. A composition according to claim 49, wherein said couplers are chosen from meta-aminophenols, meta-phenylenediamines, meta-diphenols, naphthols and heterocyclic couplers.

63. A composition according to claim 62, wherein said couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one.

64. A composition according to claim 1, wherein said at least one oxidation dye is present in said composition in an amount ranging from about 0.001% to about 20% by weight relative to the total weight of said composition.

65. A composition according to claim 64, wherein oxidation dyes are present in said composition in an amount ranging from about 0.01% to about 10% by weight relative to the total weight of said composition.

66. A composition according claim 1, further comprising at least one direct dye.

67. A composition according to claim 1, wherein said medium suitable for said oxidation dyeing is chosen from water and a mixture of water and at least one organic solvent.

68. A composition according to claim 67, wherein said at least one organic solvent is chosen from $C_1$–$C_4$ alkanols, glycerol, glycols, glycol ethers and aromatic alcohols.

69. A composition according to claim 68, wherein said glycols and glycol ethers are chosen from 2-butoxyethanol, propylene glycol, propylene glycol monomethyl ether, diethylene glycol monoethyl ether and diethylene glycol monomethyl ether.

70. A composition according to claim 69, wherein said aromatic alcohols are chosen from benzyl alcohol and phenoxy ethanol.

71. A composition according to claim 1, wherein said medium suitable for said oxidation dyeing is present in said composition in an amount ranging from 1% to 40% by weight relative to the total weight of said composition.

72. A composition according to claim 71, wherein said medium suitable for said oxidation dyeing is present in said composition in an amount ranging from about 5% to about 30% by weight relative to the total weight of said composition.

73. A composition according to claim 1 having a pH ranging from about 3 to about 11.

74. A composition according to claim 73, wherein said pH ranges from about 4 to about 9.

75. A composition according to claim 1, further comprising at least one suitable additive chosen from anionic surfactants, cationic surfactants, nonionic surfactants, amphoteric surfactants, zwitterionic surfactants, cationic polymer, nonionic polymer, amphoteric polymer, zwfiterionic polymers, inorganic thickeners, organic thickeners, antioxidants, penetrating agents, sequestering agents, fragrances, buffers, dispersants, conditioners, film-forming agents, ceramides, preserving agents and opacifiers.

76. A composition according to claim 1 in the form of a liquid, a cream, a mousse, a gel or in any other form suitable for at least one keratinous fibre.

77. A composition according to claim 76, wherein said composition form may optionally be pressurized.

78. A composition for oxidation dyeing of keratinous fibres comprising:
(a) at least one oxidation dye; and
(b) at least one enzymatic system comprising (i) at least one sol-gel matrix and at least one enzyme and optionally (ii) at least one donor for said at least one enzyme, wherein said at least one enzyme is chosen from:
(i) 2-electron oxidoreductases;
(ii) 4-electron oxidoreductases; and
(iii) peroxidases,
wherein said at least one oxidation dye and said at least one enzymatic system are immobilized in at least one sol-gel matrix;
with the proviso that when said at least one enzyme is chosen from 2-electron oxidoreductases, said at least one enzymatic system comprises at least one donor for said at least one enzyme; and
with the proviso that when said at least one enzyme is chosen from peroxidases, said at least one enzymatic system further comprises at least one source of hydrogen peroxide chosen from hydrogen peroxide and at least one enzymatic system which generates hydrogen peroxide in situ;
in a medium suitable said oxidation dyeing.

79. A process for oxidation dyeing of at least one keratinous fibre comprising applying to said at least one keratinous fibre for a time and at a temperature sufficient to achieve a desired coloration, at least one composition comprising:
(a) at least one oxidation dye; and
(b) at least one enzymatic system comprising (i) at least one enzyme immobilized in at least one sol-gel matrix and optionally (ii) at least one donor for said at least one enzyme, wherein said at least one enzyme is chosen from:
(i) 2-electron oxidoreductases;
(ii) 4-electron oxidoreductases; and
(iii) peroxidases;
with the proviso that when said at least one enzyme is chosen from 2-electron oxidoreductases, said at least one enzymatic system comprises at least one donor for said at least one enzyme, and
with the proviso that when said at least one enzyme is chosen from peroxidases, said at least one enzymatic system further comprises at least one source of hydrogen peroxide chosen from hydrogen peroxide and at least one enzymatic system which generates hydrogen peroxide in situ,
in a medium suitable said oxidation dyeing.

80. A process according to claim 79, wherein said at least one composition is a ready-to-use composition.

81. A process according to claim 79, further comprising the step of rinsing said composition from said fibres.

82. A process according to claim 81, further comprising the step of washing the fibres.

83. A process according to claim 82, further comprising the step of rinsing said fibres a second time.

84. A process according to claim 83, further comprising the step of drying said fibres.

85. A process according to claim 79, wherein said time sufficient to achieve a desired colouration ranges from about 1 to about 60 minutes.

86. A process according to claim 85, wherein said time sufficient to achieve a desired colouration ranges from about 5 to about 30 minutes.

87. A process according to claim 79, wherein said temperature sufficient to achieve a desired colouration ranges from room temperature to about 60° C.

88. A process according to claim 87, wherein said temperature sufficient to achieve a desired colouration ranges from room temperature to about 45° C.

89. A process according to claim 88, wherein said temperature sufficient to achieve a desired colouration ranges from about 20° C. to about 37° C.

90. A process according to claim 79, wherein said at least one keratinous fibre is a human keratinous fibre.

91. A process according to claim 90, wherein said human keratinous fibre is hair.

92. A process according to claim 79, wherein said at least one composition is chosen from ready-to-use compositions.

93. A process according to claim 79, wherein said at least one oxidation dye and said at least one enzymatic system are immobilized in the at least one sol-gel matrix.

94. A process according to claim 79, wherein said at least one enzyme is chosen from 4-electron oxidoreductases and said at least one enzyme is combined with said at least one oxidation dye.

95. A process according to claim 79, wherein said sol-gel matrix is derived from at least one sol-gel reaction of at least one precursor at a temperature suitable for said at least one sol-gel reaction, said at least one sol-gel reaction comprising (i) at least one hydrolysis reaction chosen from partial and total, acidic and basic hydrolysis reactions, and (ii) at least one condensation reaction.

96. A process according to claim 95, wherein said temperature suitable for said at least one sol-gel reaction ranges from about 10° C. to about 85° C.

97. A process according to claim 96, wherein said temperature suitable for said at least one sol-gel reaction ranges from about 20° C. to about 40° C.

98. A process according to claim 95, wherein said at least one precursor is chosen from metallic precursors wherein said metallic precursors are chosen from:
(i) oxides of transition metals, wherein said oxides of transition metals are chosen from oxides of transition metals of groups 1b to 7b of the Periodic Table, oxides of transition metals of group 8 and oxides of transition metals of the Lanthanide group of the Periodic Table;
(ii) aluminum oxides, boron oxides, silicon oxides and tin oxides; and
(iii) aluminum phosphates.

99. A process according to claim 95, wherein said at least one precursor is chosen from organometallic precursors, wherein said organometallic precursors are chosen from:
(1) silanes, titanates, and zirconates of formulae (Ia), (Ib), (Ic) and (Id):

(Ia)

(Ib)

(Ic)

(Id)

wherein:
M is chosen from silicon cations, titanium cations and zirconium cations;

$R_1$ is chosen from linear and branched alkyl groups;

R and R', which may be identical or different, are each chosen from linear and branched $C_1$–$C_{30}$ alkyl groups, $C_3$–$C_{30}$ cycloalkyl groups, aryl groups, $C_4$–$C_{30}$ aralkyl groups and $C_4$–$C_{30}$ alkylaryl groups, wherein said groups may optionally be substituted with at least one group chosen from amino groups, carboxyl groups and hydroxyl groups;

(2) chelated titanates of formula (II) and chelated zirconates of formula (II):

$$N(OR1)_n(X)x \qquad (II)$$

wherein:

N is chosen from $Ti^{a+}$ and $Zr^{a+}$, wherein:

a is chosen from 4 and 6;

X, which may be identical or different, are each chosen from chelating groups, wherein:

the degree of complexation of said chelating groups with said N is b;

wherein:

b is chosen from 2 and 3;

$R_1$, which may be identical or different, are each chosen from linear and branched alkyl groups;

x is 1 or 2; and n is equal to (a-bx), with the proviso that n is greater than or equal to 1; and (3) chelated titanates of formulae (IIIa), (IIIb) and (IIIc) and chelated zirconates of formulae (IIIa), (IIIb) and (IIIc):

$$R\text{—}N(OR_1)_m(X)_t \qquad (IIIa)$$
$$(X)_t(R_1O)_m N\text{—}R''\text{—}N(OR_1)_m(X)_t \qquad (IIIb)$$
$$(R)(R')N(OR_1)_p(X)_t \qquad (IIIc)$$

wherein:

N is chosen from $Ti^{a+}$ and $Zr^{a+}$, wherein a is chosen from 4 and 6;

X, which may be identical or different, are each chosen from chelating groups, wherein:

the degree of complexation of said chelating groups with said N is b, wherein b is chosen from 2 and 3;

$R_1$, which may be identical or different, are each chosen from linear and branched alkyl groups;

R and R', which may be identical or different, are each chosen from linear and branched $C_1$–$C_{30}$ alkyl groups, $C_3$–$C_{30}$ cycloalkyl groups, aryl groups, $C_4$–$C_{30}$ aralkyl groups and $C_4$–$C_{30}$ alkylaryl groups, wherein said groups may optionally be substituted with at least one group chosen from amino groups, carboxyl groups and hydroxyl groups;

R" is a divalent group derived from linear and branched $C_1$–$C_{30}$ alkyl groups, $C_3$–$C_{30}$ cycloalkyl groups, aryl groups, $C_4$–$C_{30}$ aralkyl groups and $C_4$–$C_{30}$ alkylaryl groups, wherein said divalent group may optionally be substituted with at least one group chosen from amino groups, carboxyl groups and hydroxyl groups;

t is chosen from 1 and 2, except in IIIc, t may only be 1;

m is equal to (a-bt-1), with the proviso that m is greater than or equal to 1; and p is equal to (a-bt-2), with the proviso that p is greater than or equal to 1.

100. A process according to claim 99, wherein said $R_1$ is chosen from linear and branched $C_1$–$C_4$ alkyl groups.

101. A process according to claim 99, wherein said chelating groups are chosen from carboxylic acids, β-ketones, β-diketones, β-keto esters, β-keto amines, α-hydroxy acids, β-hydroxy acids, amino acids, salicylic acid and derivatives of any of the foregoing.

102. A process according to claim 101, wherein said chelating groups are chosen from acetoacetoxyethyl methacrylate, methyl α-hydroxymethacrylate, ε-N-methacryloyl-L-lysine, 4-ethacrylaminosalicylic acid and 5-methacrylaminosalicylic acid.

103. A process according to claim 95, wherein said at least one precursor is chosen from tetraalkoxysilanes, alkyltrialkoxysilanes and aminoalkyltrialkoxysilanes.

104. A process according to claim 95, wherein said at least one sol-gel matrix further comprises at least one additional optionally functionalized polymer.

105. A process according to claim 104, wherein said at least one sol-gel matrix comprises at least one polymer network, chosen from partially crosslinked polymer networks and totally crosslinked polymer networks, derived from said at least one sol-gel reaction of said at least one precursor and at least one additional optionally functionalized polymer.

106. A process according to claim 105, wherein said at least one additional optionally functionalized polymer is chosen from polymers derived from radical polymerization of at least one monomer and polymers derived from polycondensation of at least one monomer.

107. A process according to claim 79, wherein said 2-electron oxidoreductases, which may be identical or different, are each chosen from pyranose oxidases, glucose oxidases, glycerol oxidases, lactate oxidases, pyruvate oxidases, uricases, choline oxidases, sarcosine oxidases, bilirubin oxidases and amino acid oxidases.

108. A process according to claim 107, wherein said uricases are chosen from uricases of animal origin, microbial origin and those uricases derived from biotechnology.

109. A process according to claim 107, wherein said uricases are chosen from uricases extracted from boar's liver, uricases derived from *Arthrobacter globiformis* and uricases derived from *Aspergillus flavus*.

110. A process according to claim 79, wherein said 2-electron oxidoreductases, which may be identical or different, are present in said composition in an amount ranging from about 0.01% to about 20% by weight relative to the total weight of said composition.

111. A process according to claim 110, wherein said 2-electron oxidoreductases, which may be identical or different, are present in said composition in an amount ranging from about 0.1% to about 10% by weight relative to the total weight of said composition.

112. A process according to claim 79, wherein said 2-electron oxidoreductases, which may be identical or different, are present in said composition in an amount ranging from about 10 U to about $10^8$ U units per 100 g of dye composition.

113. A process according claim 79, wherein said 4-electron oxidoreductases, which may be identical or different, are chosen from laccases, tyrosinases, catechol oxidases, deamino oxidases and polyphenol oxidases.

114. A process according to claim 113, wherein said 4-electron oxidoreductases, which may be identical or different, are each chosen from laccases of plant origin, animal origin, fungal origin and bacterial origin and laccases obtained by biotechnology.

115. A process according to claim 114, wherein said laccases are chosen from those produced by plants performing chlorophyll synthesis.

116. A process according to claim 114, wherein said laccases are chosen from any of the laccases which may be extracted from Anacardiacea, Podocarpacea, *Rosmarinus off.*, *Solanum tuberosum*, Iris sp., Coffea sp., *Daucus carrota*, *Vinca minor*, *Persea americana*, *Catharanthus roseus*, Musa sp., *Malus pumila, Gingko biloba, Monotropa hypopithys*, Aesculus sp., *Acer pseudoplatanus, Prunus persica* and *Pistacia palaestina*.

117. A process according to claim 114, wherein said laccases are chosen from those of fungal origin and those obtained by biotechnology.

118. A process according to claim 117, wherein said laccases are chosen from *Polyporus versicolor, Rhizoctonia praticola, Rhus vernicifera*, Scytalidium, *Polyporus pinsitus, Myceliophthora thermophila, Rhizoctonia solani, Pyricularia orizae, Trametes versicolor, Fomes fomentarius, Chaetomium thermophile, Neurospora crassa, Colorius versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants of any of the foregoing.

119. A process according to claim 114, wherein said laccases are present in said composition in an amount ranging from about 0.5 lacu to 2000 lacu units per 100 g of said composition.

120. A process according to claim 114, wherein said laccases are present in said composition in an amount ranging from about 10,000 U to about $4 \times 10^7$ U units per 100 g of said composition.

121. A process according to claim 114, wherein said laccases are present in said composition in an amount ranging from about 20 ulac to about $2 \times 10^6$ ulac units per 100 g of said composition.

122. A process according to claim 79, wherein said 4-electron oxidoreductases are present in said composition in an amount ranging from about 0.01% to about 20% by weight relative to the total weight of said composition.

123. A process according to claim 122, wherein said 4-electron oxidoreductases are present in said composition in an amount ranging from about 0.1% to about 10% by weight relative to the total weight of said composition.

124. A process according claim 79, wherein said peroxidases, which may be identical or different, are each chosen from NADH peroxidases, fatty acid peroxidases, NADPH peroxidases, cytochrome-c peroxidases, iodide peroxidases, chloride peroxidases, L-ascorbate peroxidases and glutathione peroxidases.

125. A process according to claim 79, wherein said peroxidases, which may be identical or different, are each chosen from simplex peroxidases and catalases.

126. A process according to claim 125, wherein said peroxidases, which may be identical or different, are each chosen from simplex peroxidases.

127. A process according to claim 79, wherein said peroxidases, which may be different or identical, are each chosen from peroxidases of animal origin, plant origin, fungal origin bacterial origin and those peroxidases obtained by biotechnology.

128. A process according to claim 127, wherein said peroxidases, which may be identical or different, are each chosen from peroxidases extracted from apples, peroxidases extracted from apricots, peroxidases extracted from barleys, peroxidases extracted from black radishes, peroxidases extracted from beetroots, peroxidases extracted from cabbages, peroxidases extracted from carrots, peroxidases extracted from corns, peroxidases extracted from cottons, peroxidases extracted from garlics, peroxidases extracted from grapes, peroxidases extracted from mints, peroxidases extracted from rhubarbs, peroxidases extracted from soybeans, peroxidases extracted from spinach, peroxidases extracted from inky cap, peroxidases extracted from cow's milk and peroxidases extracted from microorganisms.

129. A process according to claim 79, wherein said peroxidases, which may be different or identical, are present in said composition in an amount ranging from about 0.0001% to about 20% by weight relative to the total weight of said composition.

130. A process according to claim 129, wherein said peroxidases, which may be different or identical, are present in said composition in an amount ranging from about 0.001% to about 10% by weight relative to the total weight of said composition.

131. A process according to claim 95, wherein said at least one sol-gel reaction further comprises at least one step chosen from addition of at least one cosmetically acceptable organic solvent and dissolving said at least one precursor in at least one cosmetically acceptable organic solvent optionally comprising water.

132. A process according to claim 131, wherein said at least one cosmetically acceptable organic solvent is chosen from lower $C_1$–$C_4$ alcohols, propylene glycol, propylene glycol esters, propylene glycolethers, ethylene glycol, ethylene glycol esters, ethylene glycol ethers, acetone, methyl ethyl ketone, methyl acetate, ethyl acetate, butyl acetate, glycerol, volatile hydrocarbon oils, non-volatile hydrocarbon oils, volatile silicones and non-volatile silicones.

133. A process according to claim 132, wherein said lower $C_1$–$C_4$ alcohols are chosen from ethanol.

134. A process according to claim 132, wherein said volatile hydrocarbon oils are chosen from Isopars isoparaffins and isododecane.

135. A process according to claim 132, wherein said volatile silicones are chosen from cyclomethicones and hexamethyldisiloxanes.

136. A process according claim 79, wherein said at least one oxidation dye is chosen from oxidation bases, couplers and acid addition salts of any of the foregoing.

137. A process according to claim 136, wherein said acid addition salts are chosen from hydrochlorides, hydrobromides, sulphates, tartrates, lactates and acetates.

138. A process according to claim 136, wherein said oxidation bases are chosen from para-phenylenediamines, double bases, para-aminophenols and heterocyclic bases.

139. A process according to claim 138, wherein said para-phenylenediamines are chosen from compounds having formula (IV) and the acid addition salts thereof:

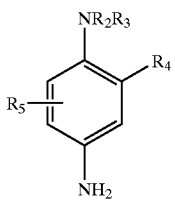

(IV)

wherein:
- $R_2$ and $R_3$, which may be identical or different, are each chosen from hydrogen atoms, $C_1-C_4$ alkyl groups and $C_1-C_4$ monohydroxyalkyl groups;
- $R_4$ is chosen from hydrogen atoms, halogen atoms, $C_1-C_4$ alkyl groups and $C_1-C_4$ monohydroxyalkyl groups; and
- $R_5$ is chosen from hydrogen atoms and $C_1-C_4$ alkyl-groups.

140. A process according to claim 139, wherein said para-phenylenediamines of formula (IV) are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine and N-ethyl-N-(β-hydroxyethyl)-para-phenylenediamine.

141. A process according to claim 138, wherein said double bases are chosen from compounds of formula (V) and the acid addition salts thereof:

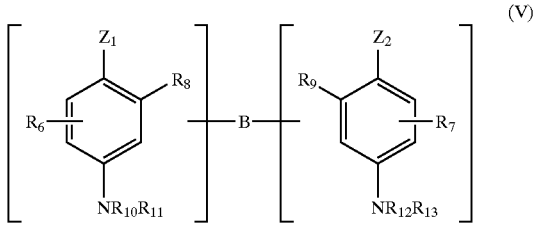

(V)

wherein:
- $Z_1$ and $Z_2$, which may be identical or different, are each chosen from hydroxyl groups and —$NH_2$ groups which optionally may be substituted with at least one group chosen from $C_1-C_4$ alkyl groups and linking arms B;
- $R_6$ and $R_7$, which may be identical or different, are each chosen from hydrogen atoms, halogen atoms, $C_1-C_4$ alkylgroups, $C_1-C_4$ monohydroxyalkylgroups, $C_2-C_4$ polyhydroxyalkylgroups, $C_1-C_4$ aminoalkylgroups and linking arms B;
- $R_8$, $R_9$, $R_{10}$, $R_{11}$, $R_{12}$ and $R_{13}$, which may be identical or different, are each chosen from hydrogen atoms, $C_1-C_4$ alkylgroups and linking arms B; and
- the linking arms B are chosen from linear and branched, divalent alkylene groups comprising from 1 to 14 carbon atoms, which may optionally be interrupted by and may optionally end with at least one group chosen from nitrogen-containing groups and hetero atoms, and which may optionally be substituted with at least one group chosen from hydroxyl groups and $C_1-C6$ alkoxygroups;

with the proviso that said compounds of formula (V) comprise only one linking arm B per molecule.

142. A process according to claim 141, wherein said hetero atoms are chosen from oxygen atoms, sulphur atoms and nitrogen atoms.

143. A process according to claim 141, wherein said nitrogen-containing groups are chosen from amino groups, mono($C_1-C_4$)alkylamino groups, di($C_1-C_4$)alkylamino groups, tri($C_1-C_4$)alkylamino groups, monohydroxy ($C_1-C_4$)alkylamino groups, imidazolinium groups and ammonium groups.

144. A process according to claim 143, wherein said double bases of formula (V) are chosen from N,N'-bis(β-hydroxyethyl)-N,N'-bis(4'-aminophenyl)-1,3-diaminopropanol, N,N'-bis(β-hydroxyethy)-N,N'-bis(4'-aminohenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane.

145. A process according to claim 144, wherein said double bases of formula (V) are chosen from N,N'-bis(β-hydroxyethyl)-N,N'-bis(4'-aminophenyl)-1,3-diaminopropanol and 1,8-bis(2,5-diaminophenoxy)-3,5-dioxaoctane.

146. A process according to claim 138, wherein said para-aminophenols are chosen from compounds of formula (VI) and the acid addition salts thereof:

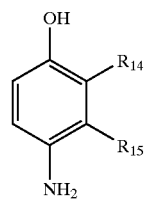

(VI)

wherein:
- $R_{14}$ and $R_{15}$, which may be identical or different, are each chosen from hydrogen atoms, halogen atoms, $C_1-C_4$ alkyl groups, $C_1-C_4$ monohydroxyalkyl groups, ($C_1-C_4$)alkoxy($C_1-C_4$)alkyl groups, $C_1-C_4$ aminoalkyl groups and monohydroxy($C_1-C_4$)alkylamino($C_1-C_4$) alkyl groups;

with the proviso that at least one of said $R_{14}$ and said $R_{15}$ is a hydrogen atom.

147. A process according to claim 146, wherein said para-aminophenols of formula (VI) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and 4-amino-2-fluorophenol.

148. A process according to claim 138, wherein said heterocyclic bases are chosen from pyridine derivatives, pyrimidine derivatives and pyrazole derivatives.

149. A process according to claim 136, wherein said couplers are chosen from meta-aminophenols, meta-phenylenediamines, meta-diphenols, naphthols and heterocyclic couplers.

150. A process according to claim 149, wherein said couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl-amino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one.

151. A process according to claim 79, wherein said at least one oxidation dye is present in said composition in an amount ranging from about 0.001% to about 20% by weight relative to the total weight of said composition.

152. A process according to claim 151, wherein oxidation dyes are present in said composition in an amount ranging from about 0.01% to about 10% by weight relative to the total weight of said composition.

153. A process according claim 79, further comprising at least one direct dye.

154. A process according to claim 79, wherein said medium suitable for at least one keratinous fibre is chosen from water and a mixture of water and at least one organic solvent.

155. A process according to claim 154, wherein said at least one organic solvent is chosen from $C_1$–$C_4$ alkanols, glycerol, glycols, glycol ethers and aromatic alcohols.

156. A process according to claim 155, wherein said glycols and glycol ethers are chosen from 2-butoxyethanol, propylene glycol, propylene glycol monomethyl ether, diethylene glycol monoethyl ether and diethylene glycol monomethyl ether.

157. A process according to claim 156, wherein said aromatic alcohols are chosen from benzyl alcohol and phenoxy ethanol.

158. A process according to claim 79, wherein said medium suitable for at least one keratinous fibre is present in said composition in an amount ranging from about 1% to about 40% by weight relative to the total weight of said composition.

159. A process according to claim 158, wherein said medium appropriate for keratinous fibres is present in said composition in an amount ranging from about 5% to about 30% by weight relative to the total weight of said composition.

160. A process according to claim 79, wherein said composition has a pH ranging from about 3 to about 11.

161. A process according to claim 160, wherein said pH ranges from about 4 to about 9.

162. A process according to claim 79, wherein said composition further comprises at least one suitable additive chosen from anionic surfactants, cationic surfactants, nonionic surfactants, amphoteric surfactants, zwitterionic surfactants, cationic polymer, nonionic polymer, amphoteric polymer, zwitterionic polymers, inorganic thickeners, organic thickeners, antioxidants, penetrating agents, sequestering agents, fragrances, buffers, dispersants, conditioners, film-forming agents, ceramides, preserving agents and opacifiers.

163. A process according to claim 79, wherein said composition is in the form of a liquid, a cream, a mousse, a gel or in any other form suitable for at least one keratinous fibre.

164. A process according to claim 163, wherein said composition form may optionally be pressurized.

165. A process for oxidation dyeing of keratinous fibres comprising applying to said keratinous fibres for a time and at a temperature sufficient to achieve a desired coloration, at least one composition comprising:
  (a) at least one oxidation dye; and
  (b) at least one enzymatic system comprising (i) at least one enzyme and optionally (ii) at least one donor for said at least one enzyme, wherein said at least one enzyme is chosen from:
    (i) 2-electron oxidoreductases;
    (ii) 4-electron oxidoreductases; and
    (iii) peroxidases,
wherein said at least one oxidation dye and said at least one enzymatic system are immobilized in at least one sol-gel matrix;
  with the proviso that when said at least one enzyme is chosen from 2-electron oxidoreductases, said at least one enzymatic system comprises at least one donor for said at least one enzyme; and
  with the proviso that when said at least one enzyme is chosen from peroxidases, said at least one enzymatic system further comprises at least one source of hydrogen peroxide chosen from hydrogen peroxide and at least one enzymatic system which generates hydrogen peroxide in situ;
in a medium suitable for said oxidation dyeing.

166. A process for dyeing keratinous fibres comprising:
  (a) storing, in the absence of air, at least one composition comprising:
    (a) at least one oxidation dye; and
    (b) at least one enzymatic system comprising (i) at least one sol-gel matrix and at least one enzyme immobilized in said at least one sol-gel matrix and optionally (ii) at least one donor for said at least one enzyme, wherein said at least one enzyme is chosen from:
      (i) 2-electron oxidoreductases;
      (ii) 4-electron oxidoreductases; and
      (iii) peroxidases;
    in a medium suitable for said oxidation dyeing,
      with the proviso that when said at least one enzyme is chosen from 2-electron oxidoreductases, said at least one enzymatic system comprises at least one donor for said at least one enzyme, and
      with the proviso that when said at least one enzyme is chosen from peroxidases, said at least oneenzymatic system further comprises at least one source of hydrogen peroxide chosen from hydrogen peroxide and at least one enzymatic system which generates hydrogen peroxide in situ; and
  (b) applying said at least one composition to said keratinous fibres in the presence of air and for a time and at a temperature sufficient to develop a desired coloration.

167. A process according to claim 166, wherein said temperature sufficient to develop a desired coloration ranges from room temperature to about 45° C.

168. A process according to claim 166, wherein said time sufficient to develop a desired coloration ranges from about 1 to about 60 minutes.

169. A process according to claim 166, wherein said time sufficient to develop a desired coloration ranges from about 5 to about 30 minutes.

170. A process according to claim 166, wherein said at least one keratinous fibre is a human keratinous fibre.

171. A process according to claim 170, wherein said human keratinous fibre is hair.

172. A process for dyeing at least one keratinous fibre comprising:
(a) storing, in the absence of air, at least one sol-gel matrix comprising at least one composition comprising:
  (a) at least one oxidation dye; and
  (b) at least one enzymatic system comprising (i) at least one sol-gel matrix and at least one enzyme immobilized in said at least one sol-gel matrix and optionally (ii) at least one donor for said at least one enzyme, wherein said at least one enzyme is chosen from:
    (i) 2-electron oxidoreductases;
    (ii) 4-electron oxidoreductases; and
    (iii) peroxidases;
    with the proviso that when said at least one enzyme is chosen from 2-electron oxidoreductases, said at least one enzymatic system comprises at least one donor for said at least one enzyme, and
    with the proviso that when said at least one enzyme is chosen from peroxidases, said at least one enzymatic system further comprises at least one source of hydrogen peroxide chosen from hydrogen peroxide and at least one enzymatic system which generates hydrogen peroxide in situ;
(b) dispersing said at least one sol-gel matrix in a medium suitable for at least one keratinous fibre; and
(c) applying said at least one sol-gel matrix dispersed in said medium suitable for at least one keratinous fibre to said at least one keratinous fibre in the presence of air and for a time and at a temperature sufficient to develop a desired coloration.

173. A process for dyeing at least one keratinous fibre comprising:
(a) storing a first composition;
(b) storing a second composition separately from said first composition and said third composition;
(c) optionally storing a third composition separately from said first composition and said second composition;
(d) mixing said first composition, said second composition and optionally said third composition to form a mixture in the presence of air; and
(e) applying said mixture to said keratinous fibres for a time and at a temperature sufficient to develop a desired coloration.

174. A multicompartment device or dyeing kit comprising:
(a) a first compartment comprising a first composition; and
(b) a second compartment comprising a second composition;
wherein said first compartment comprises at least one oxidation dye in a medium suitable for said oxidation dyeing and optionally at least one suitable donor for said peroxidases, and
wherein said second compartment comprises at least one enzymatic system comprising (i) at least one sol-gel matrix and at least one enzyme immobilized in said at least one sol-gel matrix and optionally (ii) at least one donor for said at least one enzyme, wherein said at least one enzyme is chosen from:
  (i) 2-electron oxidoreductases;
  (ii) 4-electron oxidoreductases; and
  (ii) peroxidases;
in a medium suitable for said oxidation dyeing,
with the proviso that when said at least one enzyme is chosen from 2-electron oxidoreductases, said at least one enzymatic system comprises at least one donor for said at least one enzyme, and
with the proviso that when said at least one enzyme is chosen from peroxidases, said at least one enzymatic system further comprises at least one source of hydrogen peroxide chosen from hydrogen peroxide and at least one enzymatic system which generates hydrogen peroxide in situ, in a medium suitable for said oxidation dyeing.

175. A multicompartment device or dyeing kit comprising:
(a) a first compartment comprising a first composition;
(b) a second compartment comprising a second composition; and
(c) a third compartment comprising a third composition;
wherein said first compartment comprises at least one oxidation dye in a medium suitable for said oxidation dyeing,
wherein said second compartment comprises at least one enzymatic system comprising (i) at least one sol-gel matrix and at least one enzyme immobilized in said at least one sol-gel matrix chosen from 2-electron oxidoreductases and (ii) hydrogen peroxide or at least one enzymatic system which generates hydrogen peroxide in situ, in a medium suitable for said oxidation dyeing, and
wherein said third compartment comprises at least one donor for said at least one enzyme for said at least one enzyme.

176. A multicompartment device or dyeing kit comprising:
(a) a first compartment comprising a first composition;
(b) a second compartment comprising a second composition; and
(c) a third compartment comprising a third composition;
wherein said second compartment comprises at least one enzymatic system comprising at least one 2-electron oxidoreductase immobilized in at least one sol-gel matrix, at least one peroxidase immobilized in at least one sol-gel matrix and optionally at least one suitable donor, in a medium suitable for said oxidation dyeing and
wherein said third compartment comprises at least one donor for at least one enzyme chosen from 2-electron oxidoreductase donors and peroxidase donors, in a medium suitable for said oxidation dyeing wherein said first compartment comprises at least one oxidation dye and optionally at least one donor for said at least one enzyme, in a medium suitable for said oxidation dyeing.

177. A multicompartment device or dyeing kit comprising:
(a) a first compartment comprising a first composition;
(b) a second compartment comprising a second composition; and
(c) a third compartment comprising a third composition;
wherein said first compartment comprises at least one oxidation dye and optionally at least one suitable donor, in a medium suitable for said oxidation dyeing,
wherein said second compartment comprises at least one sol-gel matrix and at least one enzymatic system comprising at least one peroxidase immobilized in said at least one sol-gel matrix and optionally at least one donor for said at least one peroxidase, in a medium suitable for said oxidation dyeing, and wherein said third compartment comprises at least one source of hydrogen peroxide in a medium suitable for said oxidation dyeing.

178. A multicompartment device or dyeing kit according to claim 177, wherein said at least one source of hydrogen peroxide is chosen from (i) 2-electron oxidoreductases immobilized in at least one sol-gel matrix and at least one donor for said 2-electron oxidoreductases and (ii) hydrogen peroxide solutions.

179. A process according to claim 127, wherein said microorganisms are chosen from *Acetobacter peroxidans, Staphylococcus faecalis* and Arthromycesramosus.

180. A composition according to claim 13, wherein said chelating groups are chosen from β-hydroxyamino acids.

181. A process according to claim 101, wherein said chelating groups are chosen from β-hydroxyamino acids.

\* \* \* \* \*

UNITED STATES PATENT AND TRADEMARK OFFICE
CERTIFICATE OF CORRECTION

PATENT NO. : 6,730,133 B1  Page 1 of 3
DATED : May 4, 2004
INVENTOR(S) : Grégory Plos et al.

It is certified that error appears in the above-identified patent and that said Letters Patent is hereby corrected as shown below:

Title page, Item [54] and Column 1, line 3,
Title, "DYING" should read -- DYEING --.

Column 21,
Line 59, "according claim" should read -- according to claim --.

Column 22,
Line 5, "chosen any" should read -- chosen from any --.
Lines 51, 60 and 63, "according claim" should read -- according to claim --.
Line 66, "origin bacterial" should read -- origin, bacterial --.

Column 23,
Line 55, "according claim" should read -- according to claim --.

Column 24,
Lines 19-20, "alkyl-groups." should read -- alkyl groups. --.
Line 60, "alkylgroups, $C_1$-$C_4$ monohydroxyalkylgroups, $C_2$-$C_4$" should read -- alkyl groups, $C_1$-$C_4$ monohydroxyalkyl groups, $C_2$-$C_4$ --.
Line 61, "polyhydroxyalkylgroups, $C_1$-$C_4$ aminoalkylgroups and" should read -- polyhydroxyalkyl groups, $C_1$-$C_4$ aminoalkyl groups and --.
Line 63, "$R_{12}$and" should read -- $R_{12}$ and --.
Line 65, "alkylgroups" should read -- alkyl groups --.

Column 25,
Lines 5-6, "alkoxy-groups;" should read -- alkoxy groups; --.

Column 26,
Line 24, "according claim" should read -- according to claim --.
Lines 58-59, "zwifterionic" should read -- zwitterionic --.

Column 27,
Lines 25 and 51, "suitable said" should read -- suitable for said --.

Column 29,
Line 12, "N(OR1)$_n$(X)x" should read -- N(OR$_1$)$_n$(X)$_x$ --.

Column 30,
Line 59, "according claim" should read -- according to claim --.

UNITED STATES PATENT AND TRADEMARK OFFICE
CERTIFICATE OF CORRECTION

PATENT NO. : 6,730,133 B1
DATED : May 4, 2004
INVENTOR(S) : Gregory Plos et al.

It is certified that error appears in the above-identified patent and that said Letters Patent is hereby corrected as shown below:

Column 31,
Line 43, "2x1 0$^6$" should read -- $2x10^6$ --.
Line 53, "according claim" should read -- according to claim --.

Column 32,
Line 1, "origin bacterial" should read -- origin, bacterial --.
Line 54, "according claim" should read -- according to claim --.

Column 33,
Lines 18-19, "alkyl-groups." should read -- alkyl groups. --.
Line 60, "alkylgroups, $C_1$-$C_4$ monohydroxyalkylgroups, $C_2$-$C_4$" should read -- alkyl groups, $C_1$-$C_4$ monohydroxyalkyl groups $C_2$-$C_4$ --.
Line 61, "polyhydroxyalkylgroups, $C_1$-$C_4$ aminoalkylgroups, and" should read polyhydroxyalkyl groups, $C_1$-$C_4$ aminoalkyl groups and --.
Line 65, "alkylgroups" should read -- alkyl groups --.

Column 34,
Line 5, "$C_1$-C6" should read -- $C_1$-$C_6$ --.
Line 6, "alkoxygroups;" should read -- alkoxy groups; --.
Line 21, "aminohenyl)ethylenediamine," should read
-- aminophenyl)ethylenediamine, --.

UNITED STATES PATENT AND TRADEMARK OFFICE
CERTIFICATE OF CORRECTION

PATENT NO. : 6,730,133 B1
DATED : May 4, 2004
INVENTOR(S) : Gregory Plos et al.

It is certified that error appears in the above-identified patent and that said Letters Patent is hereby corrected as shown below:

Column 35,
Line 23, "according claim" should read -- according to claim --.

Column 36,
Lines 49-50, "oneenzymatic" should read -- one enzymatic --.

Signed and Sealed this

Twenty-seventh Day of July, 2004

JON W. DUDAS
*Acting Director of the United States Patent and Trademark Office*